(12) United States Patent
Wilson et al.

(10) Patent No.: US 8,687,865 B2
(45) Date of Patent: Apr. 1, 2014

(54) TELEMETRIC ORTHOPAEDIC IMPLANT

(75) Inventors: Darren James Wilson, York (GB); Stephen James Guy Taylor, Middlesex (GB); Ian McCarthy, London (GB)

(73) Assignee: Smith & Nephew, Inc., Memphis, TN (US)

( * ) Notice: Subject to any disclaimer, the term of this patent is extended or adjusted under 35 U.S.C. 154(b) by 110 days.

(21) Appl. No.: 13/382,454

(22) PCT Filed: Jul. 6, 2010

(86) PCT No.: PCT/GB2010/001298
§ 371 (c)(1),
(2), (4) Date: Mar. 15, 2012

(87) PCT Pub. No.: WO2011/004151
PCT Pub. Date: Jan. 13, 2011

(65) Prior Publication Data
US 2012/0163683 A1 Jun. 28, 2012

(30) Foreign Application Priority Data
Jul. 6, 2009 (GB) .................................. 0911697.1

(51) Int. Cl.
*G06K 9/00* (2006.01)
*A61B 17/56* (2006.01)
*A61B 17/58* (2006.01)
*A61B 17/88* (2006.01)

(52) U.S. Cl.
USPC .............. 382/128; 606/62; 606/102; 606/281

(58) Field of Classification Search
USPC ......... 382/128, 129, 130, 131, 132, 133, 134; 600/25, 30, 377; 606/53, 62, 79, 102, 606/300, 916; 424/171; 128/920, 922
See application file for complete search history.

(56) References Cited

U.S. PATENT DOCUMENTS 7,347,874 B2 *   3/2008   Disilvestro .................. 623/18.12

* cited by examiner

*Primary Examiner* — Abolfazl Tabatabai
(74) *Attorney, Agent, or Firm* — Krieg DeVault LLP

(57) ABSTRACT

The invention relates generally to orthopaedic implants, and more particularly to orthopaedic implants having data acquisition capabilities and their use in monitoring and diagnosing fracture healing. RSA is also disclosed as a method for measuring inter-fragmentary movement in long bone fractures in order to confirm whether the fracture is reduced and for detecting changes in stiffness of the healing callus.

17 Claims, 39 Drawing Sheets

42-A2

42-C2

42-A1

43-A3

42-A2

42-C2

42-A1

43-A3

(i)  (ii)

Torque fractured bone

—✕— Torque intact

◆ Ax.force fractured bone

■ Ax.force intact (a)

(b)

(c)

(d)

TELEMETRIC ORTHOPAEDIC IMPLANT

CROSS REFERENCE TO RELATED APPLICATIONS

This application is a United States National Phase filing of International Application No. PCT/GB2010/001298 filed on Jul. 6, 2010 which claims priority from GB provisional application No. 0911697.1 filed on Jul. 6, 2009, both of which are herein incorporated in their entirety.

FIELD OF THE INVENTION

The invention relates generally to orthopaedic implants, and more particularly to orthopaedic implants having data acquisition capabilities and their use in monitoring and diagnosing fracture healing.

BACKGROUND TO THE INVENTION

Fractures of long bones are a prevalent problem, accounting for 10% of non-fatal injuries in the USA (Kanakaris 2007). Of these, the most common are fractures of the tibial shaft, approximated to result in 77,000 hospitalisations a year in the USA (Schmidt et al 2003). The epidemiology and aetiology of tibial shaft fractures indicates a relation with risk behaviour. This type of fracture appears to be most prevalent in young men (Grutter 2000). A study by Court-Brown, 1995 found the mean age of patients with tibial shaft fractures to be 37 years, with the highest incidence occurring amongst teenage males. The two most common causes being; sports related injuries and road traffic accidents. There are several classifications described for fractures of the tibia, perhaps the most widely accepted of long bone fracture classifications in the AO/OTA classification (Arbeitsgemeinschaft für Osteosynthesefragen/Orthopaedic Trauma Association). This classification system looks solely at the pattern of fracture, not taking into consideration the local soft tissue damage (FIG. 1). Associated soft tissue injury may be classified according to the Tscherne and Gotzen classification (Schmidt et al 2003) for closed tibial fractures, and according to the Gustilo Anderson classification (Gustilo & Anderson 1976) for open fractures.

For an in-vitro biomechanical study of an instrumented nail, used for strain telemetry, the most useful of these classifications is the AO classification. This is an alphanumeric classification system for all long bone fractures. An example of a fracture classified in this way is 42-C2. "4" represents the tibia, whilst the "2" tells us this is a fracture of the diaphysis. Having described the location, the letters A, B or C are assigned to indicate the fracture type and increasing complexity. Subgroups of these, in increasing severity, are assigned by the addition of the numbers 1, 2 or 3 (Grutter 2000). Further subdivisions of these groups may be made, to indicate the number of fragments.

Of the various fracture, 42-A3 appears to be the most common, accounting for 23.9% of tibial diaphyseal fractures (Court-Brown 1995).

Treatment of these fractures is broadly divided into two categories, conservative and surgical. Conservative therapy involved the use of a plaster-cast or functional bracing. Surgical treatment can involve either open-reduction and internal fixation (ORIF) of intramedullary (IM) nailing. A META-analysis comparing conservative treatment to ORIF found that despite significantly decreased risk of superficial wound infection, casting resulted in a lower rate of union at 20 weeks (p=0.008) (Littenburg et al. 1998). Additionally casting is limited by the severity of the fracture and deformity, with initial moderate or severe displacement increasing the rate of delayed of non-union from 9% to as much as 27% (Schmidt et al 2003).

IM nailing appears to be the preferred method of treatment for the majority of tibial fractures (Schmidt et al 2003). This suggestion is supported by a Randomised Control Trial (RCT) which shows IM nailing to result in faster union and a decrease in the rates of malunion, in comparison to conservative treatment (Hooper G J 1991).

Delayed or non-union are a major concern with tibial fractures. On a "best case scenario" calculation the cost of one tibial non-union is estimated to be £16,330, with 20% being direct costs of treatment and 80% due to indirect costs (Kanakaris 2007). The reported incidence of delayed union shows a great degree of variability due to the arbitrary definitions used. Generally delayed union of the tibia is recognised at 20 weeks, however, earlier detection may be possible. One could think of delayed union as the point at which altering the treatment may be considered, in order to achieve union (Phieffer & Goulet 2006). The definition of non-union is broadly accepted as the presence of no radiographic evidence of healing for three consecutive months, in a fracture of at least 9 months of age. The prevalence of delayed and non-union is reported to be 4.4% and 2.5% respectively. However, in open fractures, delayed union may be as high as 41%, requiring further treatment before union is achieved (Phieffer & Goulet 2006).

Treatment for delayed union varies in light of the cause. This can, broadly speaking, involve stabilisation, re-nailing, bone-grafts, adjunct therapy such as electrical stimulation, ultrasound or biological adjuncts such as Bone Morphogenic Protein (BMP). However timing is key to success as early diagnosis and treatment of delayed union can save the patient from considerable periods of disability and pain (Phieffer & Goulet 2006), whilst also having an impact on health economics due to a reduction in morbidity.

Various methods have been used to ascertain the end point of healing of fractures. This is fundamental knowledge to clinicians so as to advise patients on appropriate load bearing in the injured limb or to diagnose the risk of delayed or non-unions.

Currently there is a lack of a gold standard method which supplies sensitive data, good repeatability as well as ease of use. Serial radiographs and manual manipulation, often used in conjunction, are subjective and show inter-clinician variability. The inaccuracy and complexity of using dexa-scans, vibrational analysis, scintigraphy and ultrasound has also eliminated them as potential measurement tools.

Telemetry

An IM nail acts to provide stability, whilst transmitting rotational, bending and compressive forces across the fracture site and maintaining anatomical alignment of the bone. The IM nail also acts as a load sharing device, gradually shifting the load to the bone, as it heals.

Telemetry enables the direct measurement of strain and load carried by an appropriately instrumented IM and hence gives an indication of the progress of fracture repair without disrupting fracture healing. An example of a telemetric orthopaedic system is disclosed in WO 2007/025191, which is herein incorporated in its entirety. In addition to its clinical use, such methodology proves to be of great benefit toward increasing our understanding of fracture healing and its biomechanics. It allows optimisation of post-operative patient care, assessing the role of different activities on skeletal loads to identify which are most appropriate for providing the desired mechanical environment (Schneider E, 2001).

Strain gauges, which enable the direct measurement of the load applied to the nail, are conventionally located in multiple recesses in the outer wall of the nail and hence have the potential to cause changes in the biomechanical properties of the nail. This in turn could lead to local weakening or stress concentration.

We have identified redundancy associated with the provision of strain gauges at multiple locations on a nail and have identified: firstly an optimal position for a recess comprising a plurality of strain gauges and secondly an optimal orientation of the strain gauges relative to the longitudinal axis of the nail. The strain gauges are capable of monitoring the strain in a nail when it experiences either off-set axial compression, torsional forces or three/four point bending forces.

The identification of the optimal positioning and orientation of the strain gauges will facilitate the generation of a single commercial design of an IM nail which can be used with varying fracture patterns.

Radiostereometric Analysis (RSA)

In vivo measurement of three-dimensional (3D) displacement of prosthetics or body parts was pioneered by Gam Selvik in 1974 (Bragdon et al 2002). RSA is also referred to as radiostereometry or roentgen stereophotogrammic analysis.

RSA measurements can be obtained using pairs of simultaneous radiographs taken repeatedly over time. Tantalum bead markers are implanted into the body part or implant segment under study with at least three non-colinear beads needed to define each rigid body subject to scrutiny (Valstar et al. 2005). A 3D coordinate system is achieved by way of a calibration cage embedded with tantalum beads in well defined, immoveable positions. Two radiographs placed side-by-side, in a uniplanar arrangement or at a 90 degree angle to each other, in the case of a bi-planar arrangement (Valstar et al. 2005) are used to establish the 3D coordinates of the markers, and displacement between the rigid bodies can be calculated (Madanat et al. 2006) using commercially available RSA software systems.

Whilst RSA is a "gold standard" technique for assessing fixation and migration of joint replacements and determining micromotion of the bone, this technique has not be considered for measuring inter-fragmentary movement in long bone fractures fixated with an orthopaedic fixation device.

We have identified that RSA can be used accurately and precisely to measure inter-fragmentary movement in a long bone, such as a tibia, fixated with an IM nail before and after reduction of the fracture.

SUMMARY OF THE INVENTION

According to a first aspect of the invention there is provided a telemetric orthopaedic implant system, the system comprising:
(a) an orthopaedic implant, the orthopaedic implant having a longitudinal axis and comprising
  (i) a strain gauge orientated at about +45° and/or at about −45° relative to the longitudinal axis of the implant;
  (ii) a recess adapted to receive said strain gauge(s);
  (iii) an electronic component electrically connected to at least a power supply, a first transmitter, a first receiver, and a first microprocessor;
  (iv) a recess adapted to receive said electronic components;
  (v) potting material to seal said recess;
  (vi) a power source electrically connected to said electronic component.
(b) a control unit, the control unit comprising;
  (i) a second microprocessor
  (ii) a second transmitter electrically connected to said second microprocessor, the second transmitter adapted to send a signal to said first receiver of said electronic component; and
  (iii) a second receiver electrically connected to said second microprocessor, the second receiver adapted to receive data from said transmitter of said electronic component.

The gauges orientated at about +45° or at about −45° relative to the longitudinal axis of the orthopaedic implant have been identified as being optimally positioned to measure strain associated with either torque and also three- or four-point bending. The relative location of the gauges to the fracture site has been found to be unimportant when measuring strain upon application of torque.

In embodiments of the invention further strain gauges are provided which are orientated either at about 0° or about 90° relative to the longitudinal axis of the orthopaedic implant. Such orientation has been identified as being optimal for measuring strain associated with offset-axial loading. However, the relative location of the gauges to the fracture site has been found to be important and there is a significant diminishment in sensitivity in strain measurement when the fracture site is distal to the gauge.

It is therefore desirable in a commercial embodiment of a nail to provide gauges which are capable of measuring strain regardless of fracture type and location and to provide healthcare personnel with options relating to the mechanical loading regime to be utilised. For example, off-set axial compression loading requires the patient to be ambulatory.

Whilst a commercial IM nail could therefore be provided with gauges orientated at about +45° and or about −45° relative to the longitudinal axis of the orthopaedic implant this would limit the loading regime to torque, which may not be satisfactory or possible with some patients. The potential for an IM nail to offer an alternative to torque loading ie. off-set axial compression or three- or four point bending by the provision of differently orientated gauges in one recess is therefore viewed as an attractive commercial offering that will not prejudice the mechanical integrity of the IM nail.

Commercial embodiments of the nail have a recess which comprises a strain gauge orientated at about +45° and a strain gauge orientated at about 0°, or a strain gauge orientated at about +45° and a strain gauge orientated at about 90°, or a strain gauge orientated at about −45° and a strain gauge orientated at about 0°, or strain gauge orientated at about −45° and a strain gauge orientated at about 90°.

In embodiments of the invention the recess comprises a strain gauge orientated at +45°, a strain gauge orientated at about −45° and a strain gauge located at about 0°, or a strain gauge orientated at about +45°, a strain gauge orientated at about −45° and a strain gauge orientated at about 90°, or a strain gauge orientated at about +45°, a strain gauge orientated at about 0° and a strain gauge orientated at about 90°, or a strain gauge orientated at about −45°, a strain gauge orientated at about 0° and a strain gauge orientated at about 90°.

In embodiments of the invention the recess comprises a strain gauge orientated at about +45°, a strain gauge orientated at about −45°, a strain gauge orientated at about 0° and a strain gauge orientated at about 90°.

Examples of suitable mechanical strain gauges include foil, thin film, or semiconductor strain gauges. Alternatively, the sensors may be load cells used to directly measure mechanical load.

In embodiments of the invention a lid is optionally associated with the recess to provide electrical shielding for the circuitry therein.

According to a second aspect of the invention there is provided a telemetric orthopaedic implant comprising;
(i) a strain gauge orientated at about +45° and/or −45° relative to a longitudinal axis of the implant;
(ii) a recess adapted to receive said strain gauge(s);
(iii) an electronic component electrically connected to at least a power supply, a first transmitter, a first receiver, and a first microprocessor;
(iv) a recess adapted to receive said electronic components;
(v) potting material to seal said recesses;
(vi) a power source electrically connected to said electronic component.

In embodiments of the second aspect of the invention at least one further strain gauge is orientated at about 0° and/or at about 90° relative to the longitudinal axis of the implant.

In embodiments of the invention a lid is optionally associated with the recess to provide electrical shielding for the circuitry therein.

In embodiments according to the first and second aspects of the invention the orthopaedic implant is an IM nail.

A telemetric IM nail has been previously disclosed in WO 2007/025191 which is herein incorporated, by reference, in its entirety. Suitable materials and methodology for the instrumentation of a nail and examples of suitable peripheral components for use in communication and for storing information received from the nail are disclosed in WO 2007/025191.

In embodiments of the invention the telemetric orthopaedic implant, more specifically an IM nail is provided with a single recess for receiving the strain gauges.

In specific embodiments of the invention this single recess is located in the proximal portion of the nail.

In specific embodiments of the invention this single recess comprises or consists of strain gauges orientated about +45° and about 0° or about −45° and about 0° relative to the longitudinal axis of the nail.

In alternative embodiments of the invention the recess in which the strain gauges are provided is located substantially mid-way along the length of the longitudinal axis of the IM nail.

In an alternative embodiment of the invention the strain gauge recess is located substantially mid-way along the length of the longitudinal axis and extending into the tapered proximal region of the nail. The wall thickness of the proximal region in some designs of an IM nail is slightly thicker and the provision of a recess which retains the strain gauges and the associated electronic components has less effect on the mechanical integrity of the nail than if the recess was located in other regions of the nail.

In embodiments of the invention the recess is dimensioned such that the pocket extends along the longitudinal axis of the nail and has a length greater than its width.

In embodiments of the invention the recess has a length of between about 10 and 150 mm, or between about 10 and 130 mm, or between about 100 mm and 150 mm, or between about 100 mm and 140 mm, or between about 100 mm and 130 mm, or between about 120 mm and 140 mm.

In embodiments of the invention the recess has a length of about 130 mm.

The recess has a mid-way point along its length.

In embodiments of the invention the mid-way point along the length of the recess is located approximately mid-way along the longitudinal axis of the IM nail.

In embodiments of the invention the mid-way point along the length of the recess is offset from the mid-way point of the longitudinal axis of the nail, by up to the length of the pocket. For example, the length of the recess can be defined as having a first end and a second end, and either of these ends can be located at the mid-way point along the longitudinal axis of the nail.

An example of an IM nail is the TRIGEN META NAIL® (Smith & Nephew). Due to the design constraints of the TRIGEN META NAIL®, the recess is located in the proximal region of the nail.

In embodiments of the invention the IM nail comprises or consists of the design of the 8 or 9 pocket nail disclosed in Table 1

In embodiments of the invention the IM nail is for use in repairing fractures of the long bones, for example tibial or femoral fractures.

Alternative embodiments include incorporation of the strain gauges and the other electronic components within other implantable trauma products, such as a plate, a bone screw, a cannulated screw, a pin, a rod, a staple, and a cable. Further, the instrumentation described herein is extendable to joint replacement implant, such as total knee replacements (TKR) and total hip replacements (THR), dental implants, and craniomaxillofacial implants.

According to a third aspect of the invention there is provided the use of a telemetric orthopaedic implant according to the second aspect of the invention in the system according to the first aspect of the invention.

While immobilization and surgery may facilitate bone healing, the healing of a fracture still requires adequate physiological healing which can be achieved through continuously monitoring changes in the in situ load distribution between the implant and the surrounding bone using sensors and a biotelemetry system. The mass and architecture of bone are known to be influenced by mechanical loading applied to them. In the absence of appropriate loading due to stress shielding caused by poor management of internal orthopaedic fixation systems, bone mass is reduced, resulting in compromised healing of the fracture. The primary function of a telemetric orthopaedic implant is to carry load immediately after surgical placement. For example, the telemetric orthopaedic nail carries the load immediately after surgical placement in the intrameduallary canal. With progression of fracture healing, the load sharing between the implant and the bone changes. This can be tracked by using strain gauges which are optimally positioned within the orthopaedic implant regardless of the location of the fracture is. This has the advantage that a single design of nail can be used for a range of fracture types and fracture locations. The strain gauges are used to monitor the progress of union in the case of fracture by either continuously or intermittently monitoring the load component of the healing bone in all spatial components, which is unobtainable from X-rays. Periodic follow-up will provide a graph that shows the gradual decrease of relative motion of the fragments until union occurs.

Each fracture patient generates his or her own healing curve; however the general shape of the healing curve indicates whether the fracture will progress to either a union condition, delayed union condition or a non-union condition. The healing curve generated from a patient is dependent on a number of factors including the type and location of the fracture, health status (underlying disease), age, activity, rehabilitation, and time to reach weight bearing.

According to a fourth aspect of the present invention there is provided a method of measuring applied mechanical load across an orthopaedic implant, said method comprising the steps of;
(i) positioning a subject having a telemetric orthopaedic implant according to the second aspect of the invention in a position suitable for applying a desired mechanical load;
(ii) applying the mechanical load to the implant; and
(iii) interrogating at least one strain gauge provided within the implant.

The load measured by the strain gauge can then by compared with hypothetical load vs. healing time curves showing the load distribution between an instrumented nail and the surrounding bone for (i) fractures that progress to a union condition, (iii) fractures that are a delayed non-union and (iii) fractures that maintain a non-union condition. Although fracture healing results in a reduction in implant load, the remaining load of the nail can be significant and are expected to increase with patient activity. It has been suggested that loading of the bone may increase up to 50% after implant removal. The load measured in the adjacent bone can be determined by subtracting the implant load from the load exerted through the limb, which is determined using either a force plate or balance. The clinician can also measure the load acting through the contra-lateral limb in order to provide a reference measurement for a fully functional limb.

If the surgeon observes that the strain on the implant is decreasing over time, this implies that the surrounding hard tissue (for example the callus) is accepting some of the load and thus, the fracture is healing. However, if the strain on the implant is unchanged with time and at the approximate level as when the patient was discharged from hospital or other health care facility, this implies that the surrounding hard tissue is not bearing the load and, therefore the fracture is not healing.

In embodiments of the method according to the fourth aspect of the invention there is provided a method of measuring the mechanical load across an implanted telemetric orthopaedic implant upon application of a torsional force, said method comprising the steps of;
(i) positioning a subject having the telemetric orthopaedic implant either in a stance or supine position;
(ii) applying a torsional force on the telemetric orthopaedic implant; and
(iii) interrogating a strain gauge in the about +45° and/or about −45° orientation.

In embodiments of the method according to the fourth aspect of the invention there is provided a method of measuring the mechanical load across an orthopaedic implant upon application of an off-set axial compressive force, said method comprising the steps of;
(i) positioning a subject having the telemetric orthopaedic implant in a stance position;
(ii) applying an off-set axial compressive force on the telemetric orthopaedic implant; and
(iii) interrogating a strain gauge in the about 0° and/or about 90° orientation.

In embodiments of the method according to the fourth aspect of the invention there is provided a method of measuring the mechanical load across an orthopaedic implant upon application of a three or four point bending force, said method comprising the steps of;
(i) positioning a subject having the telemetric orthopaedic implant in a stance or supine position;
(ii) applying a three or four point bending force on the telemetric orthopaedic implant; and
(iii) interrogating a strain gauge in the about +45°, about −45°, about 0° and/or about 90° orientation.

According to a fifth aspect of the present invention there is provided a method of monitoring fracture healing in a subject, said method comprising the steps of;
(i) positioning a subject having a telemetric orthopaedic implant according to the second aspect of the invention in a position suitable for applying a desired mechanical load;
(ii) applying the mechanical load;
(iii) interrogating at least one strain gauge provided within the implant;
(iv) correlating the strain with a reference fracture healing curve.

In embodiments according to the fifth aspect of the invention the mechanical load is selected from the group consisting of; off-set axial compression, torque, three point bending or four point bending, wherein the subjecting is optionally positioned in the stance or supine phase.

The IM nail can be used to detect changes in fracture callus stiffness and determine healing status of the patient. The IM nail can detect changes of at least 4.1 Nm/° in callus stiffness. It is therefore envisaged that the nail can detect delayed or non-union fracture within one month of tibial fracture fixation based on callus stiffness measurements.

According to a sixth aspect of the invention there is provided the use of radiostereometric analysis for the measurement of inter-fragmentary movement within a bone fracture, wherein the bone fracture is fixed with an orthopaedic fixation device.

In embodiments of the invention RSA can be used to differentiate between intact, reduced and non-reduced fractures.

According to a seventh aspect of the invention there is provided the use of RSA to differentiate between intact, reduced and non-reduced fractures.

According to an eighth aspect of the invention there is provided a method of measuring inter-fragmentary movement within a bone fracture, wherein the bone fracture is fixed with a fracture fixation device, said method comprising;
i) associating of a plurality of radio-opaque markers with the fractured bone and/or the fracture fixation device;
ii) positioning a calibration cage comprising a plurality of radio-opaque markers at known locations in relation to the fracture site;
iii) undertaking a radiographic examination of the fracture site, wherein the fracture site and the calibration cage are simultaneously x-rayed from at least two angles;
iv) generating a three-dimensional co-ordinate system based upon the location of the radio-opaque markers in the calibration cage;
v) comparing the three-dimensional location of the radio-opaque markers associated with the fractured bone and/or the fracture fixation device with the three-dimensional co-ordinate system.

In embodiments of the invention the fracture is of the long bones, for example the tibia or femur.

The orthopaedic device can be for example, an intramedullary nail, bone plate or external fixator, such as an Ilazorov frame.

In a specific embodiment of the invention RSA is used to accurately and precisely monitor inter-fragmentary movement in a tibial shaft fracture fixed with an IM nail.

An example of a suitable radio-opaque marker is a tantalum bead, although alternative radio-opaque makers which are suitable for use in RSA are envisaged.

Alternatively, the solder joints associated with the electronic components can be utilised as reference points for monitoring inter-fragmentary bone movement.

The radio-opaque markers are preferably associated with the proximal and distal segments of the fracture, thereby defining the rigid body segments.

At least 3 radio-opaque markers are associated with the proximal and distal segments of the fracture.

The radio-opaque markers are preferably associated with the bone and/or implant in a scattered pattern.

The orthopaedic device can be selected from, for example, an IM nail, bone plate or external fixator, such as an Ilazorov frame.

RSA is capable of measuring micromotion of the bone as a result of positional change of the implant (through loosening or dynamization of the screws), variations of the forces acting on the implant (inducible displacements) and is also capable of indirectly measuring callus stiffness. Thus, RSA can be used post-operatively to assess both implant stability and fracture reduction.

It is further envisaged that RSA can be used as an intra-operative tool for trauma fixation. The utilisation of this technique will enable the surgeon to correct implant malposition or malalignment and to ensure that the fracture is adequately reduced.

It is envisaged in further embodiments of the invention that the inventions according to one or more aspects of the invention can be combined. For example, a fracture can be fixed with an appropriately instrumented IM nail, allowing both the telemetric and radiostereometric assessment of fracture healing. Advantageously the instrumented IM nail used and the system comprising the IM nail is as defined according to the first and second aspects of the invention.

According to a ninth aspect of the invention there is provided the use of a system according to the first aspect of the invention or a telemetric orthopedic implant according to the second aspect of the invention in the in vitro analysis of fracture healing, for example biomechanical models of fracture healing, including animal models.

According to a tenth aspect of the invention there is provided a methods, devices and systems as substantially herein described with reference to the accompanying Examples, Tables and Figures.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form part of the specification, illustrate the embodiments of the present invention and together with the description serve to explain the principle of the invention. In the drawings.

DETAILED DESCRIPTION OF THE INVENTION

A "smart implant" is an implant that is able to sense its environment, apply intelligence to determine what action is required, and act on the sense information to change something in a controlled, beneficial manner. One attractive application of smart implant technology is to measure loads on an orthopaedic implant. For example, an IM nail is subjected to three types of loading: bending, torsional, and compression. These loads may be measured indirectly by measuring sensor output of a series of strain gauges mounted on the orthopaedic implant. In the case of an IM nail, diametrically apposed strain gauges mounted on the outer surfaces of the nail are subjected to tensile and compressive forces, respectively. Typically, the strain measured from the sensors is higher when the implant is loaded in bending rather than in compression.

A fundamental parameter of the strain gauge is its sensitivity to strain, expressed quantitatively as the gauge factor G, as defined in WO 2007/025191.

Incorporation of sensors and other electronic components within an implantable medical device, such as an IM nail, alters its primary function from a passive load-supporting device to a smart "intelligent" system with the ability to record and monitor patient activity and compliance.

Materials and Methods
Sawbone

A 4$^{th}$ generation composite sawbone was obtained from Sawbones® Europe AB, Malmo, Sweden. This is representative of a left tibial bone.

Aetiology of Fracture Patterns

Figure 1:
FIG. 1: Aetiology of fractures
Figure 1:
Figure 1:
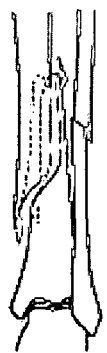
Figure 1:
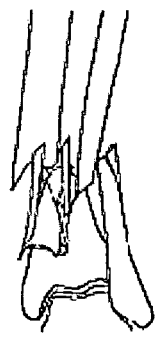

As illustrated in FIG. 1:
(i) non-reduced mid-shaft comminuted segmental fracture (42-C2);
(ii) non-reduced distal extra-articular comminuted fracture (43-A3)
(iii) reduced simple spiral fracture (42-A1)
(iv) reduced simple transverse fracture (42-A3)

IM Nail 38 cm long (10 mm outer diameter) tibial IM TRIGEN META NAIL@ (Smith & Nephew, Inc).

Instrumented IM Nail

A standard use 38 cm long, 10 mm outer diameter, tibial IMTRIGEN META NAIL® (Smith & Nephew, Inc) was used. Recesses were grooved into the surface of the nail, with dimensions 15 mm long×6 mm wide, with a 34 mm pitch. The pockets followed a spiral pattern, in an anti-clockwise direction, running down the shaft of the nail.

TABLE 1

Gauge co-ordinates for the Instrumented TRIGEN META NAIL ®

| | distance from centre of inferior proximal screw hole (mm) | | |
|---|---|---|---|
| | A (+45°) | B (0°) | C (−45°) |
| Gauge co-ordinates for 8 pocket nail | | | |
| Pocket 1 | 40 | 42.5 | 47 |
| Pocket 2 | 74 | 76.5 | 81 |
| Pocket 3 | 108 | 110.5 | 115 |
| Pocket 4 | 142 | 144.5 | 149 |
| Pocket 5 | 176 | 178.5 | 183 |
| Pocket 6 | 210 | 212.5 | 217 |
| Pocket 7 | 244 | 246.5 | 251 |
| Pocket 8 | 278 | 280.5 | 285 |
| Gauge co-ordinates for 9 pocket nail | | | |
| Pocket 1 | 40 | 42.5 | 47 |
| Pocket 2 | 72 | 74.5 | 79 |
| Pocket 3 | 104 | 106.5 | 111 |
| Pocket 4 | 136 | 138.5 | 143 |
| Pocket 5 | 168 | 170.5 | 175 |

TABLE 1-continued

Gauge co-ordinates for the Instrumented TRIGEN META NAIL ®

| | distance from centre of inferior proximal screw hole (mm) | | |
|---|---|---|---|
| | A (+45°) | B (0°) | C (−45°) |
| Pocket 6 | 200 | 202.5 | 207 |
| Pocket 7 | 232 | 234.5 | 239 |
| Pocket 8 | 264 | 266.5 | 271 |
| Pocket 9 | 296 | 298.5 | 303 |

Figure 2:
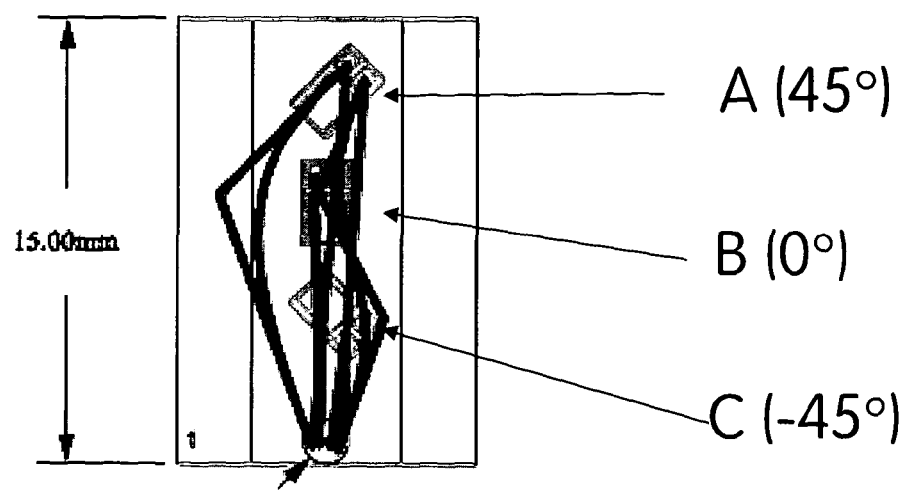
FIG. 2 CC spiral pocket arrangement in an anti-clockwise direction
Figure 3:
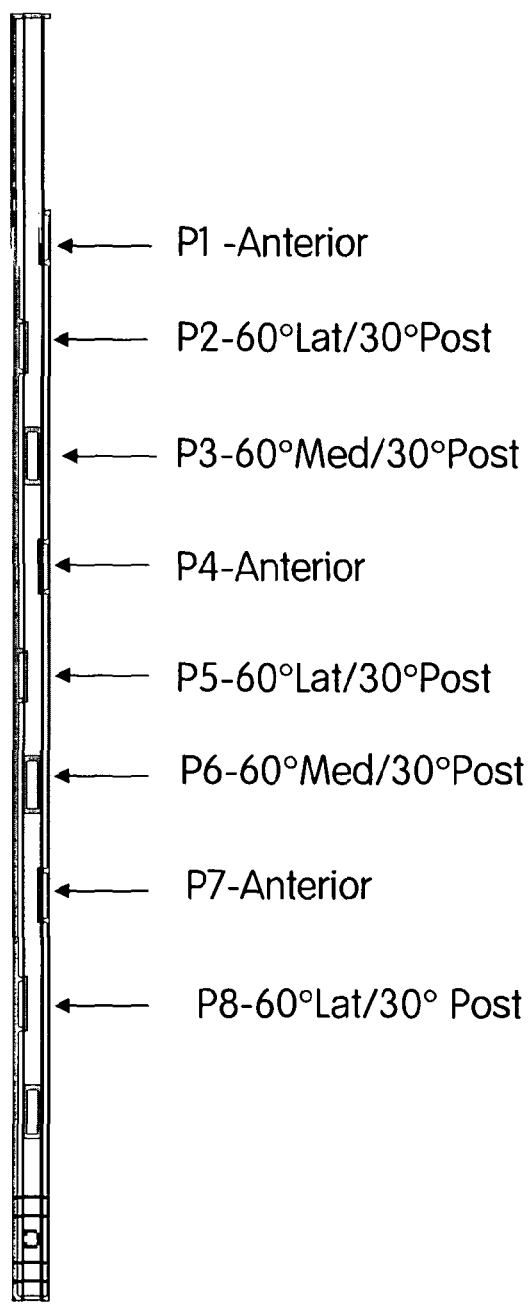
FIG. 3: Pocket locations on the TRIGEN META® nail

There are three anterior pockets (1,4,7), two medial pockets (3,6) and three lateral pockets (2,5,8). Each pocket had a hole at its base to pass 4 wires from 3 gauges through to the cannulation. The wires ran down to the distal end of the nail, inside the canal. The wires exited through the most proximal of the distal screw holes and ran along an angled channel machined to avoid the two alternative screw holes, and down to the end of the nail. Three foil strain gauges (N3K-XX-S022H-50C/DP), Vishay Ltd, were bonded to the base of each pocket using MBond-600 adhesive as per FIGS. 2 and 3. The gauges are orientated relative to the longitudinal axis. Gauge A is oriented at 45°, Gauge B in line with, and Gauge C at −45° respectively. The 0° gauge detects flexion and extension, whilst the +45° and −45° gauges detect lateral bend and torsion. Gauges were conformably protected with MBond-43B coating. A free length of 500 mm of wire was provided for attachment to the amplifiers.

Gauges were wired as quarter bridges with a single return wire in each pocket. The wires were attached to 8 mm diameter connectors which were able to easily pass through the reamed canal. These were attached to an amplifier, which sent the data to Labview v8®. The data from the 8 gauges in the load cell was also recorded simultaneously through the same system. Labview v8® collects 512 measurements for each of the eight strain gauges in a 5 second window. The average value is used for data analysis. The strain count can be converted to microstrain by dividing by a factor of 6.8. Electrical noise was reduced by covering all wires with grounded tin foil and grounding components such as the loading rig. Additionally, removing the mains supply to the laptop was also found to be beneficial.

A. Telemetry Methodologies

1. Measurement of Strain in an Instrumented IM Nail Under Axial and Torsional Loads 1.1 Fracture Patterns Two fracture patterns were tested; (i) 42-C2 and (ii) 43-A3

For the mid-shaft 42-C2 fracture a pair of transverse cuts were made 5 mm apart, 24 cm from the proximal end of the tibia. Another pair of cuts needed to be made 60 mm further. Removing the two 5 mm fragments allowed 3 segments to be created, the middle segment would be stabilised by the nail, with the distal and proximal segments secured by the cross screws. The fracture gaps represented the multiple fragments of the comminuted fracture. The fractures were aligned with pocket 6 at the distal end and pocket 4 at the proximal end of the instrumented IM nail.

The distal fracture was created by cutting across the bone 30 mm and 40 mm above the proximal distal screw hole. The segment produced was removed. The fracture intersected pocket 8 of the instrumented IM nail.

The IM nail was inserted into the Sawbones@ which were over-reamed by 2 mm to a diameter of 12 mm, with the canal extending to the end of the bone.

1.2 Loading Rig

Figure 4:
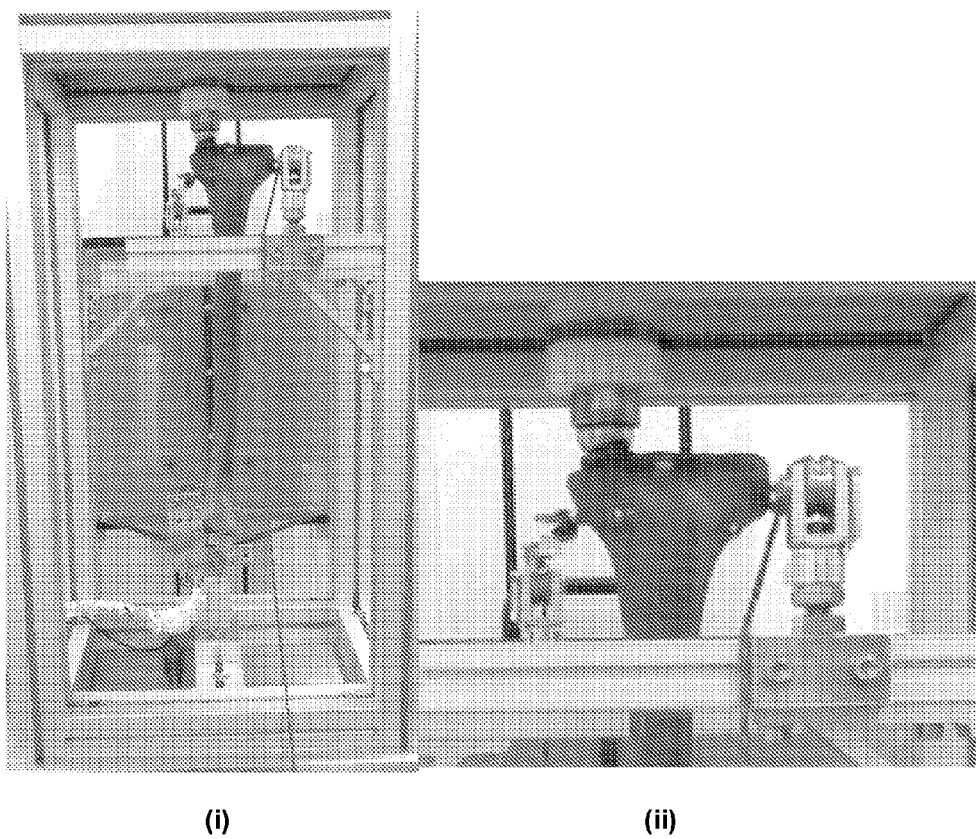
FIG. 4: Loading rig for strain measurements as a result of (i) off-set axial compression (0-1000N) and (ii) torque (±2.5 N·m)

The loading rig for the nail was constructed using an aluminium frame with an adjustable top platform, as illustrated in FIG. 4. A load cell was placed on the inferior surface, this was then mounted with an anti-torque jig, to house the distal end of the nail. It was important that the inferior surface of the nail was accessible as the hole for exit of the wires was located here.

The load cell used was designed to measure bending, internal and external torque and axial load.

The Sawbones® was loaded via two balls, at either end. An offset of 9 mm and 23 mm medial to the anatomical midline was used for load application at the distal and proximal end respectively. This offset is more representative of the mechanical line of action of the tibia (Hutson et al 1995). The proximal loading point was constructed by marking out the desired location (23 mm medial to midline), and then placing a washer over this area. The metal washer was secured using Araldite adhesive. The central hole in the metal washer was able to house the proximal ball and form the point of load transfer. Distally a small metal cap, made to size, was fitted onto the bone by fitting into two small holes created in the bone. This cap had a hole overlapping with the reamed canal of the bone, for exit of the wires, and also has a small socket for housing the distal ball, 9 mm medial to the midline. The ball communicated with the top of the load cell, with the anti-torque jig securing the distal end of the tibia in place.

1.3 Axial Load Application

Axial load application was performed via an adjustable screw fixed to the top platform. The screw was positioned to align with the loading washer on the tibia. The screw was connected to a spring, which communicated with the ball. A metal cap located around the spring guided its movement whilst providing minimal restraint. The cap was large enough to allow the ball to slide up, when the spring was under compression.

1.4 Torque Application

Torque application was performed via a pulley system. A 100 mm cross bar was passed horizontally through the proximal end of the bone, running in the medio-lateral (ML) direction. A pair of wires, able to withstand at least 10 kg of weight, were attached at the ends of the bar and passed over pulleys in the same horizontal plane. Torque was applied by hanging weights to the end of the wires. Swinging the wires over to the other side allowed for torque application in the opposite direction.

A set of plates which held both sides of the medial malleolus in place provided a method of applying anti-torque. A cross bar was inserted through the malleolus in the antero-posterior (AP) direction and running through both plates, allowed the plates to be tight enough to prevent twisting, and also prevented the plates from dislocating the bone.

Torques of up to 5 Nm were applied, in both clockwise and anti-clockwise directions by applying weights, in increments of 500 g, up to a maximum of 5 kg.

1.5 Step-by-Step Method

1 Insert nail
2 Place bone-nail construct in the loading rig
3 Connect wires to amplifier and start running Labview v8.
4 Begin loading. Torque measurement carried out at 0, 250, 500, 750 and 1000N of axial load, with increasing increments of 500 g weights being added up to 5 Kg, in both the clockwise and anti-clockwise directions. Axial load increased from 0 to 1000N in increments of 50N. When unloading the construct, only axial measurements are needed. At each loading setup a new set of data needs to be collected.
5 Remove bone and extract nail.
6 Repeated for each loading cycle.

1.6 Data Analysis

Data analysis was performed via calculation of the average strain count for each load application and then performing multiple regression with two variables. Regression was carried out with respect to axial load and torque, in order to observe the pattern of strain at the various gauges in response to these two types of loading.

2. Measurement of Strain in an Instrumented IM Nail Under Three-Point Bending

2.1 Fracture Patterns

Four fracture patterns were tested; (i) non-reduced mid-shaft comminuted segmental fracture (42-C2), (ii) non-reduced distal extra-articular comminuted fracture (43-A3), (iii) reduced simple transverse fracture (42-A3) and (iv) reduced simple spiral fracture (42-A1).

2.3 The Loading Rig

Figure 5:
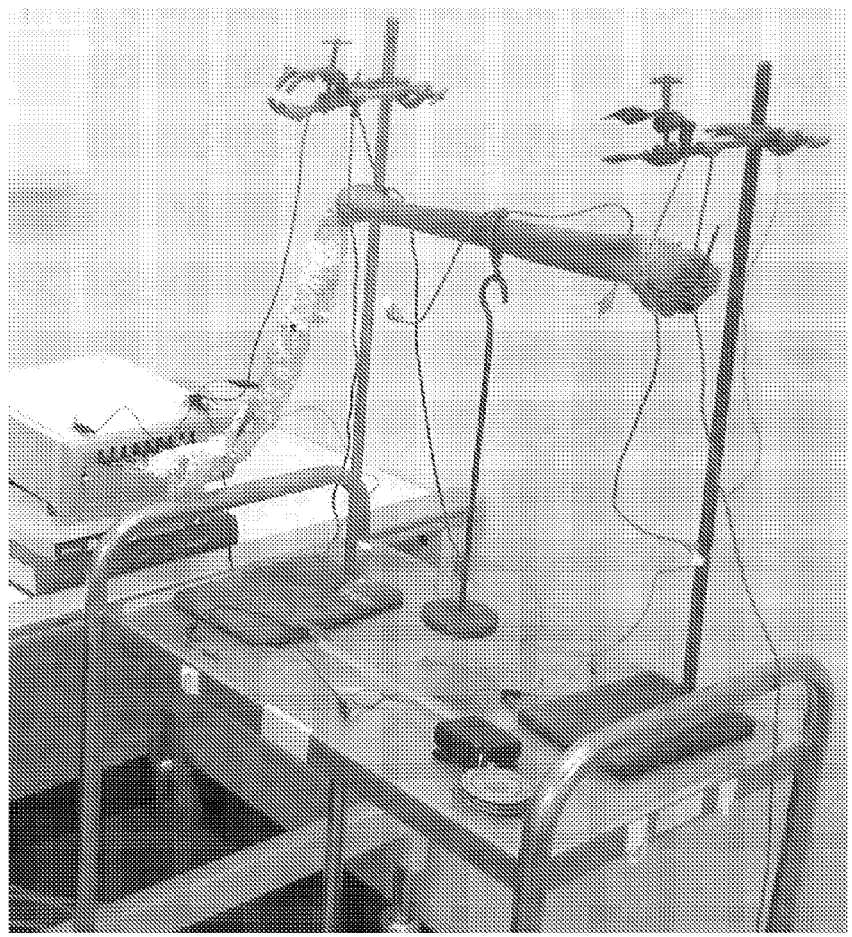
FIG. 5: Loading rig for strain measurements as a result of 3pt and 4pt bending (0-1000N)

The loading rig is illustrated in FIG. 5.

The nail-bone composite was suspended horizontally by means of two strings attached to two test tube clamps. Using a spirit level and a drill bit fixed on the bone vertically, care was taken that the nail was both perfectly horizontal and importantly that the nail's anterior surface was facing upwards and was perpendicular to the horizontal. This arrangement ensured that the 0° in-line anterior pocket gauges were perpendicular to the direction of force application and would thus be optimally positioned to detect longitudinal compression and extension of the nail. This jig enabled movement of the nail-bone composite with applied load in the X, Y and Z planes. This is because the two bone ends were not fixed rigidly. Proximally, the suspension points consisted of two screws in the medial and lateral tibial condyles. Distally, the strings attached to the protruding distal locking screws.

To apply strain to the nail-bone composite, weights were suspended from the horizontally suspended bone by means of a string and a hook. The weights were placed in five distinct positions along the length of the nail. The proximal tibial condyle screws from which the bone was suspended were the zero reference value. From this reference, the weight suspension positions in centimetres were 9, 13.5, 18, 22.5, and 27. This experimental set-up simulates rotational freedom afforded to the tibia by the collateral and cruciate ligaments at the knee joint. At each of these positions weights were added in one Kg increments starting at 0 kg, with the maximum being 10 kg. 10 kg is representative of physiological loads experienced in the tibia during the gait cycle on the basis of Wehner 2009. Therefore at each of the five positions, 11 strain count versus load measurements were taken. For each of the four fracture patterns 55 (11×5) strain count Vs load measurements were taken.

In order to assess the repeatability of the measurements, loads were applied in 1 kg increments from 0-10 kg at the mid-position (18 cm from the proximal attachment point). Strain count Vs load measurements were taken. This same process was repeated three times.

B. RSA Methodologies

3. Measurement of Inter-Fragmentary Movement in an IM Nail Fixated Tibial Fracture Under Axial and Torsional Loads Accuracy and Precision Experiments

3.1 X-Ray Energy Level Setting

A rig to load the Sawbones® was constructed from bars of aluminium, a metal which is substantially radiolucent (see FIG. 4). RSA images which were taken with the loading rig in place were carried out at 90 kV.

3.2 Radiographic Technique

The RSA set-up consisted of a calibration cage (cage 43, RSA BioMedical, Umeå, Sweden) which contained tantalum beads used to create a 3D coordinate system. The x-rays were taken on 2 AGFA CRMD4.0 General Cassettes (350 mm by 420 mm), processed in AGFA format and then sent to DICOM Link. The images were imported to UmRSA Digital Measure 6.0 where the reference and bone markers were labelled. Bone markers were always numbered as 201, 202 . . . for the proximal segment, and 301, 302 . . . for the distal segment. Data regarding kinematics were obtained from UmRSA Analysis 6.0 (RSA BioMedical, Umeå, Sweden). The kinematic data indicated migration of the distal fragment of the Sawbones® tibia relative to the proximal fragment using the "segment motion" method (displacement of segment 30 relative to segment 20).

3.3 Tantalum Beads

Spherical tantalum beads with a diameter of 0.8 mm (RSA BioMedical, Umeå, Sweden) were used as bone markers.

3.4 Accuracy and Precision Protocol for Linear Displacement

Figure 6:
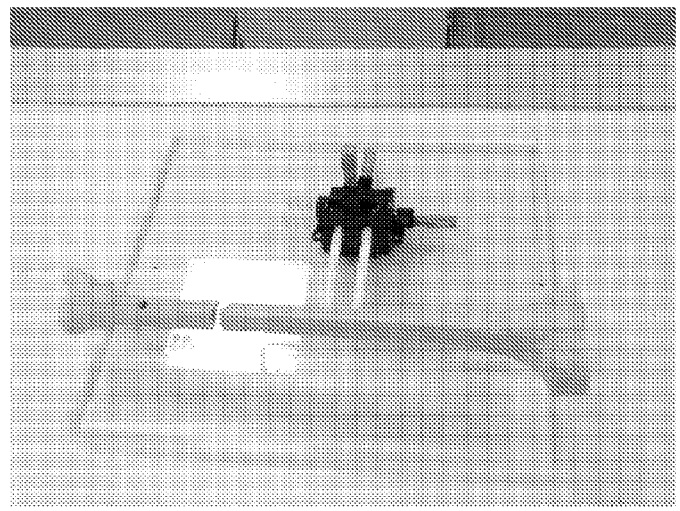
FIG. 6: Positioning of X-ray tubes in the loading rig
Figure 6:
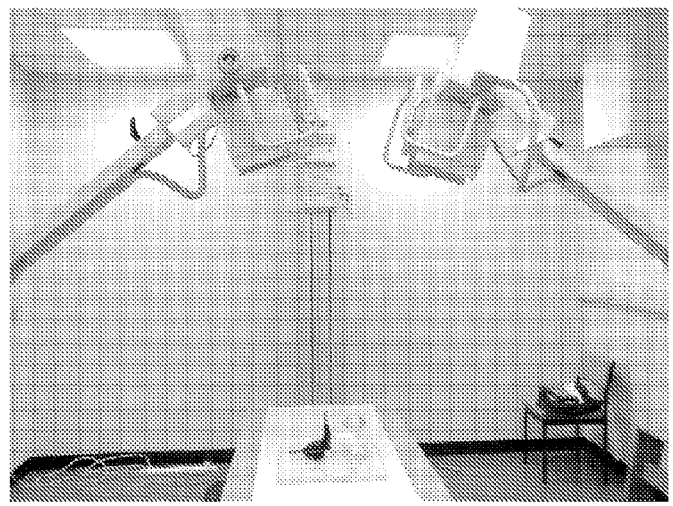

A Sawbones® with a distal third fracture gap of 1 cm was used to determine the accuracy and precision of RSA for linear displacement in the x, y, and z axes. 8 tantalum beads were inserted in the proximal and distal portions of the Sawbones®, in the areas closest to the osteotomy, using a drill and spring-loaded piston (RSA BioMedical, Umeå, Sweden). The x-ray tubes were positioned above the set-up facing downwards, as illustrated in FIG. 6. The calibration cage was placed under the radiolucent table on which the phantom model was located.

The proximal segment of the Sawbones® was attached to a high precision translation stage (M-460A-xyz, Newport, Irvine, Calif., USA), via 2 plastic pegs, in order to measure translation in the x, y and z axes. Three Vernier micrometers (model SM 13, Newport, Irvine, Calif., USA) were attached to the translation stage. This set-up, according to the Newport company, has accuracy of 1 µm for translation. The translation stage was attached to the Plexiglas base with screws. The distal segment of the Sawbones® tibia was fixed with a plastic peg to the base.

The proximal segment of the synthetic tibia was moved towards the distal segment by increments of 100 µm, with a simultaneous film pair taken at each point. The x-ray beams intersected directly over the fracture in the phantom model. This was repeated 10 times, until the proximal segment was 1 mm closer to the distal segment. An identical protocol was followed for carrying out measurements during y axis displacement, and lastly for movement in the z plane. Furthermore, five radio-pairs were taken with zero displacement. Another five were also done, each time moving the micrometer from 0 µm to 10 µm and then back to 0 µm.

3.5 Accuracy and Precision Protocol for y Rotation and Angulation (z Axis Rotation)

Figure 7:
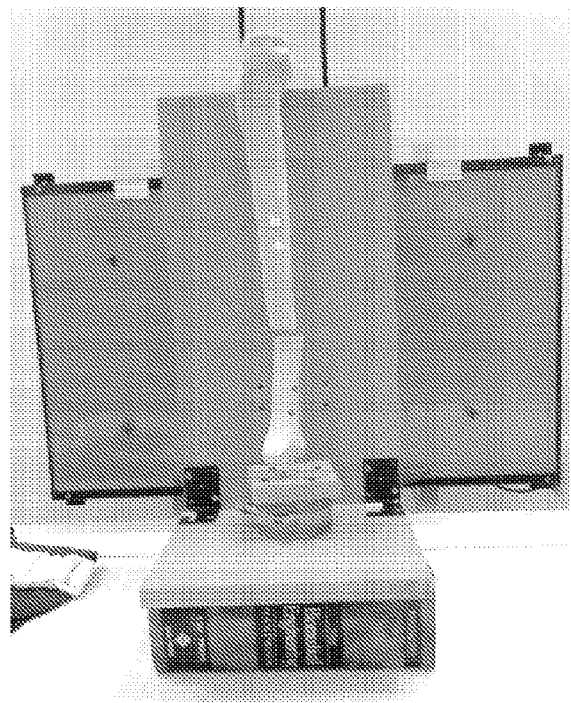
FIG. 7: A high precision rotation stage used for y axis rotation measurements
Figure 7:
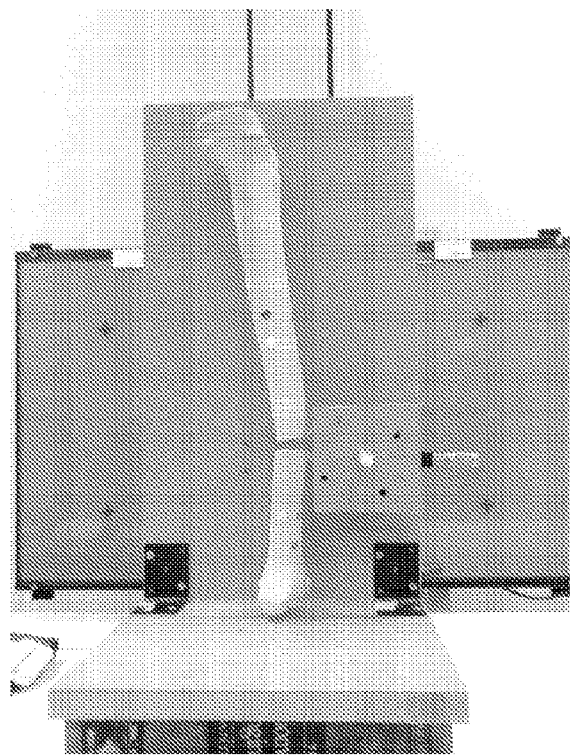

To measure accuracy and precision in y axis rotation, a high precision rotation stage was used (M-UTR-80, Newport, Irvine, Calif., USA) which was screwed to a wooden baseboard and connected to the distal segment of the Sawbones® via a wooden block and a plastic peg (FIG. 7; upper image). The accuracy of the rotation stage was $\frac{1}{60}°$. The distal segment was moved 5° clockwise, then 5° anticlockwise, with x-rays taken after every 1° of rotational movement. The proximal segment of the synthetic tibia was firmly attached to a wooden backboard with 2 plastic pegs.

For measurement of angular movement the same translation stage (FIG. 7; lower image) was used as before, but this time with only 1 Vernier micrometer. It was screwed to a wooden backboard, and it was attached to a wooden block which pushed on both segments of the Sawbones®. To simulate angular movement of a fractured tibia, both segments of the Sawbones®. were mounted on a backboard, using plastic pegs, with z axis rotation possible. A micrometer pushed the distal end of the proximal segment, and the proximal end of the distal segment, for 5 mm in the negative x direction. This was done in increments of 500 µm, up to 5 mm, and caused the segments to become more aligned in the y axis. This was done in order to establish the accuracy and precision of RSA when measuring angular motion (z axis rotation) resulting from a load applied in the medio-lateral direction.

3.6 Accuracy and Precision Calculations

Accuracy and precision were determined for overall linear displacement, as well as in each of the three planes of linear movement. Similar measurements were made for angular motion and y axis rotation.

Accuracy, the nearness of measured values to true reference values (Bragdon et al. 2002), can be determined by comparing the measured RSA displacement results with the true micrometer values using linear regression analysis, and calculating the 95% prediction interval, using SPSS (version 14.0 for Windows, Chicago, Ill.). The maximum and minimum bounds for the prediction interval can be determined, and the mean of the interval can be presented as the accuracy (Onsten et al. 2001).

Precision is the potential for the same result to be achieved on repeated occasions (Valstar et al. 2005). Precision in this study was calculated as $p=\pm(y)(SE)$ (Altman 2000). The y value was determined for a 95% confidence level, with the degree of freedom=no. of error values-1 (Bragdon et al. 2002). Error values were established by taking the true value and subtracting the measured value. This gives a total average error from which standard deviation and standard error can be determined.

Loading Experiments

3.7 Axial and Torsional Load 1000N of axial load, which was offset from the centre of the Sawbones® by 23 mm medially at the proximal end and 9 mm at the distal end, mimicked the resultant force experienced by the tibia during peak loading in the single leg stance interval of the gait cycle (Hutson et al. 1995).

5 Nm of torque was applied.

3.9 Loading Protocol

Bone A

An intact Sawbones® was positioned in the loading rig. This particular Sawbones® was reamed to 12 mm, but an IM nail had been inserted and removed from it approximately 15 times previously. The tantalum beads were implanted using a drill and a spring loaded piston (RSA BioMedical, Umeå Sweden) but the Sawbones® was so hard that only 3 markers made it into the distal segment. It was possible to apply load to the synthetic tibia, and identify how much load the bone was taking, because information from the load cell in the rig, which was positioned under the distal end of the Sawbones® passed to an amplifier, and the output was interpreted using LabVIEW v8. Axial load was applied in increments of 250N, up to and including 1000N. At every level a simultaneous film pair was taken with the bone under axial loading exclusively, then axial loading with +5 Nm of torque, and finally axial loading with −5 Nm of torque. The procedure was repeated using the same nail with all 4 locking screws in place.

Bone B

An intact Sawbones® was positioned in the loading rig, with the IM nail inserted. This Sawbones® had been reamed to 12 mm with an IM nail inserted and removed once before. Tantalum beads were applied with Araldite® adhesive. Eight markers were stuck to the proximal segment but only 7 remained attached to the distal portion. The same loading protocol was followed as outlined above. The IM nail was left in place, 4 locking screws were inserted, and the procedure repeated again. The nail was then removed. An extra-articular metaphyseal complex fracture (43-A3 AO classification) was simulated by making 2 transverse cuts, 3 cm and 4 cm above the AP distal screw hole, creating a 1 cm gap. 43-A3 fractures are sub-grouped according to the number of intermediate fragments separating the distal and proximal tibial segments (AO Surgery Reference 2009). These were not replicated, however, and instead they were represented by the 1 cm gap between the two tibial pieces. The instrumented IM nail and locking screws were then re-inserted in the bone, and the same loading procedure was repeated.

Bone C

An intact Sawbones® was positioned in the loading rig. This Sawbones® had been reamed to 12 mm with an IM nail inserted and removed once before. Nine tantalum beads were glued to the proximal and distal segments of the Sawbones® with Araldite®, although two markers had to be discarded during the analysis. An IM nail was inserted with the 4 locking screws in position. Measurements were carried out as before. The screws and nail were removed and a mid-shaft complex segmental fracture (42-C2 AO classification) was simulated by making 4 transverse cuts 20.75 cm, 21.25 cm, 27.25 cm and 27.75 cm below the proximal end of the synthetic tibia. This created an intermediate segment, 6 cm in length, which was separated from both the proximal and distal segments by gaps of 5 mm. The presence of wedge fragments calls for further sub-grouping of 42-C2 fractures. In this particular scenario, however, the aim was to recreate 42-C2.1 which has no wedge fragments (AO Surgery Reference 2009). The nail and screws were re-inserted and measurements were taken under the same conditions previously outlined.

4. Measurement of Inter-Fragmentary Movement in an IM Nail Under 3-Point Loading RSA was used to determine the extent of movement in the six degrees of freedom (linear displacement and rotation in the X, Y and Z planes) at the fracture site with applied load.

Figure 8:
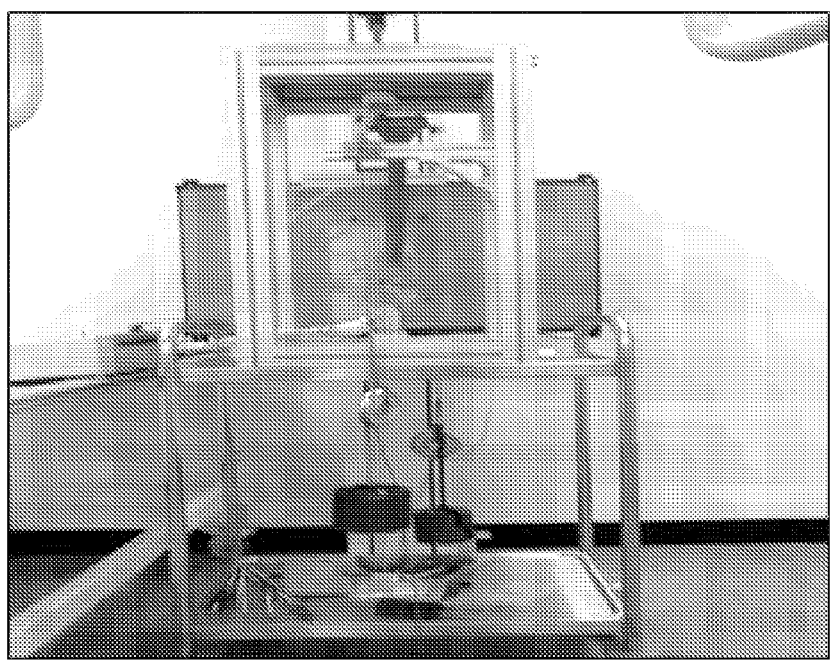
FIG. 8: Three point loading rig positioned in front of an RSA calibration cage

The 3-point loading rig was positioned in front of an RSA calibration cage (FIG. 8). A minimum of 5 tantalum beads were placed on either side of the fracture locus at a spacing consistent between all Sawbones®.

The nail-bone composite was loaded in three positions relative to the fixation point of the proximal condylar screws. The loading positions were 9, 18 and 27 cm. A 500 mg hook weight was used as the 0 kg starting point. Incremental weights of 2 kg were added until a maximum of 10 kg. At each position and for each incremental weight one digital film was taken from each of the two X-ray machines.

For each of the Sawbones® a total of 18 (3 positions×6 weights) digital films were taken, which were used to derive measurements of load versus linear and rotational displacement at the fracture site in the X, Y, Z planes.

The X-rays were processed digitally using an Agfa® processor and sent electronically to the UmRSA® processing software. By transposing the two X-rays of each measurement condition, and calibrating the tantalum beads at each fracture end against the calibration cage in 3D-space, we were able to quantify the relative displacement of the fractured bone ends with increasing load. This data was also used to calculate the stiffness of the nail-bone composite of each fracture configuration and our reinforced polyethylene tape simulated "callus".

5. Detecting Changes in Stiffness of the Sawbone® with the Instrumented Nail (Callus Simulation)

Figure 9:
FIG. 9: Callus simulation using reinforced polyethylene

The chosen method to achieve increase in stiffness across the fracture, and hence simulate callus was to apply loops of reinforced polyethylene tape across the fracture. Four different stiffnesses were simulated by applying the reinforced polyethylene tape in incremental multiples of four loops, up to a maximum of 16 loops. FIG. 9 illustrates using four loops of reinforced polyethylene tape. The width of the reinforced polyethylene tape applied was equal to the separation of the tantalum beads across the fracture. Both of those parameters were arbitrary.

The reduced 42-A3 fracture was chosen to test the nail's ability to detect changes in stiffness. The reduced fracture afforded less movement at the fracture gap and thus represented a harder challenge to the nail's detection capabilities, lending greater validity to the results.

RSA was used to determine the stiffness of the simulated "callus". Stiffness is defined as the resistance of a body to deformation (bending, stretching or compression). Mathematically it is represented as:

$$\text{stiffness} = \frac{F}{\delta}$$

F is the applied force or moment in Newtons and $\delta$ is the displacement produced by the force. The SI units are $Nm^{-1}$.

Figure 30:
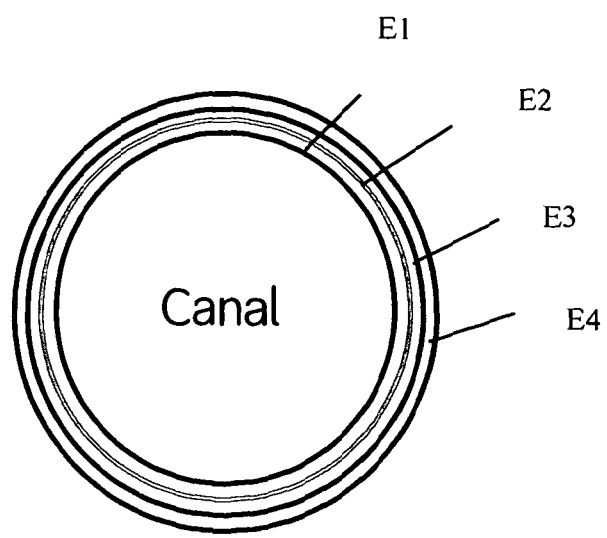
FIG. 30: Synthetic callus formation—circumferential application

C Correlation of Strain with Fracture Type, Fracture Location, Callus Maturation, Applied Load and Position of Strain Gauges (i) Formation of a Synthetic Callus As illustrated in FIG. 30, callus is composed of layers of tissue, each having a characteristic compression modulus (Lacroix et al, 2001)

E1=Granulation tissue (E=0.36 MPa)
E2=Fibrous tissue (E=1.52 MPa)
E3=Cartilage (E=11.4 MPa)
E4=Immature bone (E=1.24 GPa)

The following synthetic analogues, designed to mimic the layers of callus tissue, were layered around the bone to simulate the early stages of fracture healing:

E1=15% stainless steel (SS)+polyurethane potting compound
E2=15% hydroxyapatite (HA)+polyurethane potting compound
E3=15% tin (Sn)+polyurethane potting compound
E4=10% Beech wood shavings (BW) and Araldite 2014.

Figure 31:
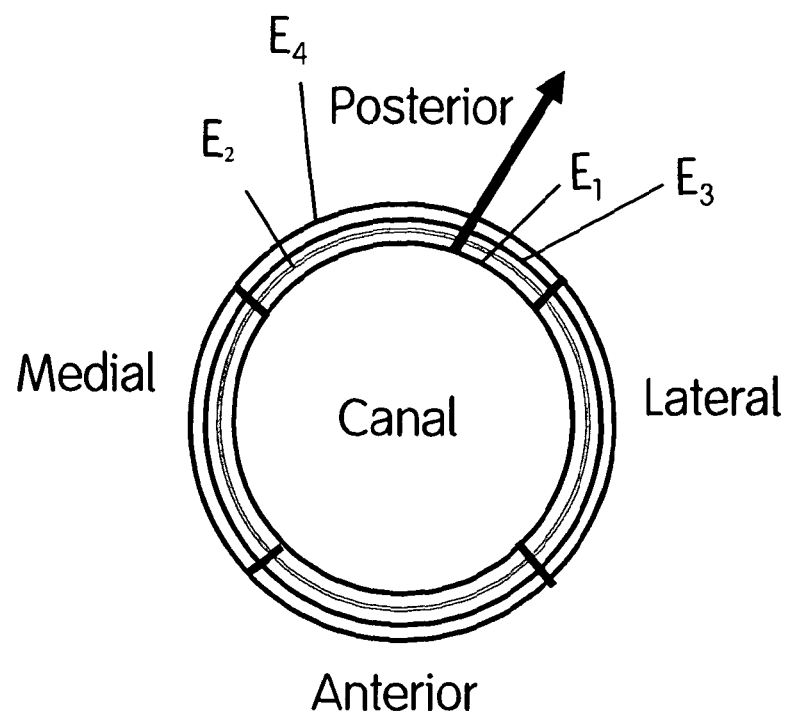
FIG. 31: Synthetic callus formation—segmental application

The layering was either circumferentially (C) (FIG. 30) or (ii) segmentally (S) in discrete quadrants (FIG. 31).

The sequence of the application of the discrete quadrants of callus growth was:
 1. External callus bridging—posterior plane; applied on day 1: layers E1-4
 2. External callus bridging—medial plane; applied on day 2: layers E1-4
 3. External callus bridging—lateral plane; applied on day 3: layers E1-4
 4. External callus bridging—anterior plane; applied on day 4: layers E1-4

(ii) Measurement of Strain/Load Applied to Instrumented Nail Versus Callus Growth/Stiffness The fracture model used was a reduced 42-A2-AO fracture.

The instrumented nail was provided with strain gauges orientated at (A) 45°, (B) 0° and/or (C) −45° either adjacent to the fracture site or remote from the fracture site.

Figure 10:
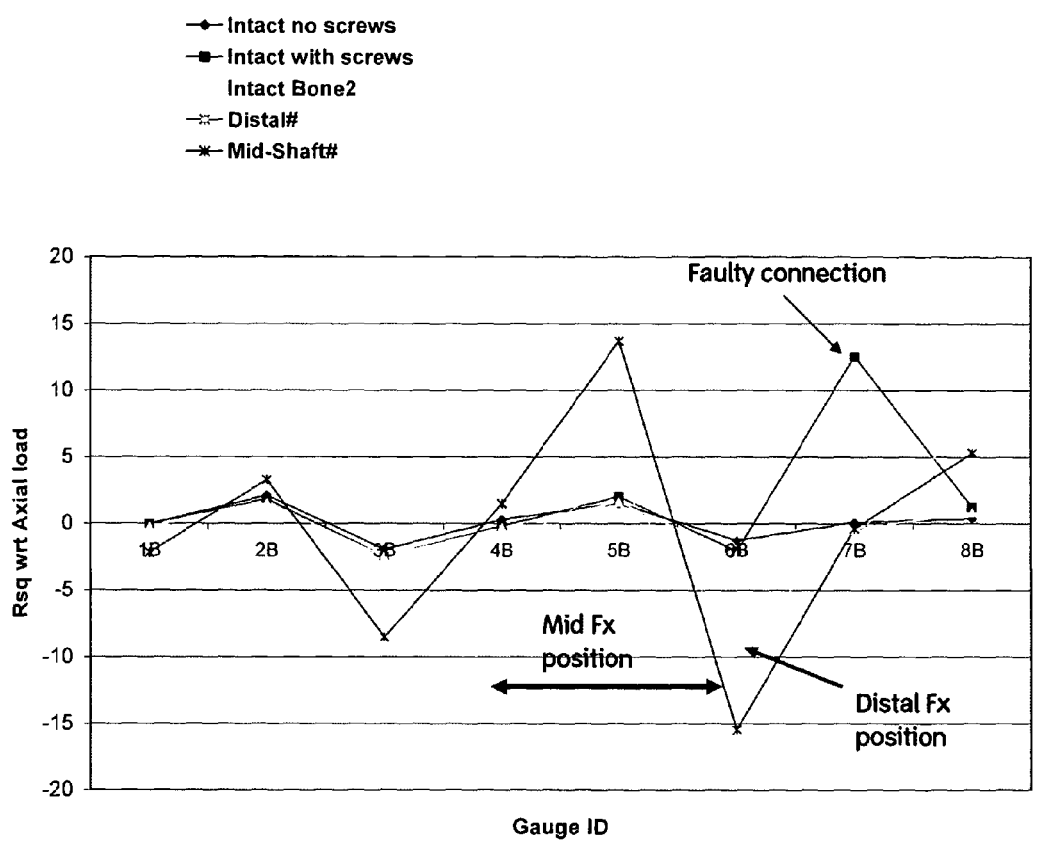
FIG. 10: Regression of strain counts in relation to axial load

The nail was subjected to the following loading patterns during the first 4-6 weeks of healing:
 stance "off axis axial compression loading"
 stance "4 point bending loading"
 torque loading 0-25 N·m at 1000N compression Results 1. Measurement of Strain in Relation to Axial and Torsional Loads in an IM Nail in a Tibial Fracture by the Use of Strain Gauges Recessed into the Nail Axial Load Gauge B is in line with (i.e 0°) the longitudinal axis of the nail and is designed to be most sensitive to strain in the axial direction. A regression of strain counts in relation to the axial load applied was carried out for each strain gauge and is shown in FIG. 10. This graph demonstrates several key concepts:

(i) the strain count was minimal in gauges on the anterior aspect of the nail (pockets 1,4&7), higher on the postero-medial gauges (pockets 2,5,8) and lower on the posterior-lateral gauges (pockets 3,6). There is a difference in strain around the circumference of the nail.

(ii) both the pattern and magnitude of strain is fairly consistent between three groups of data; intact bone with no screws, intact bone with screws and intact bone 2. There is one outlier, gauges in pocket 7B in the intact bone with screws, however this has been traced back to a faulty connection, which was repaired before any further data collection.

(iii) the two fractures showed a large deviation from the patterns observed in all three intact scenarios, with the magnitude of difference in $R^2$ being greater closer to the fracture sites.

Torque Load

Gauges A and C (orientated at +45° and −45° respectively to the longitudinal axis of the nail) were placed perpendicular to one another and were both designed to be sensitive to torque. Theoretically, their relative positioning should result in equal and opposite strain counts.

Figure 11:
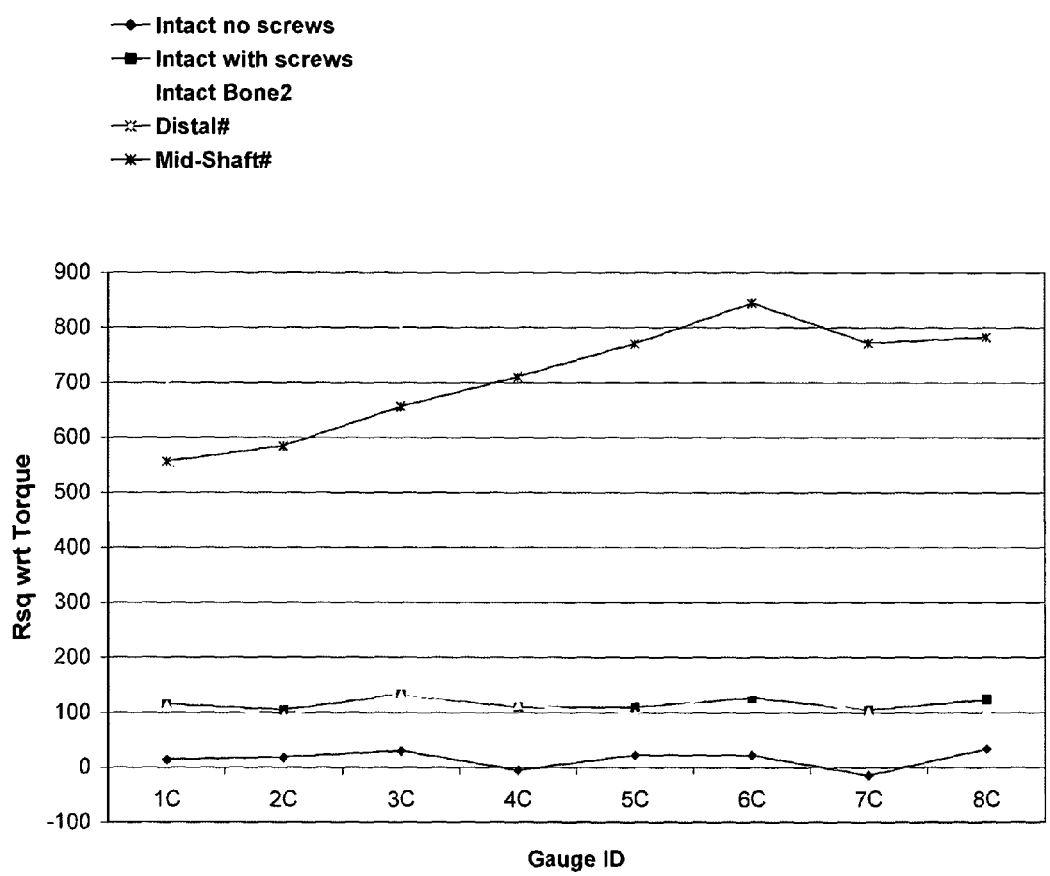
FIG. 11: Regression of strain counts in relation to torque

FIG. 11 demonstrates several key concepts:
(i) minimal strain response with non-intact, non-fixated nail
(ii) equal sharing of the strain along the length of the nail for the intact, fixated nail
(iii) increase in strain magnitude as the gauge location moves more distally with fractured bones peaking at pocket 6 for the distal mid shaft fracture
(iv) nail strain are higher in torsion than in axial compression.

Principal Strain Magnitude and Direction

Combining strain counts obtained for all 3 gauges at any given location allows the magnitude of strain and the principal direction of strain to be determined in relation to a specific gauge.

Figure 12:
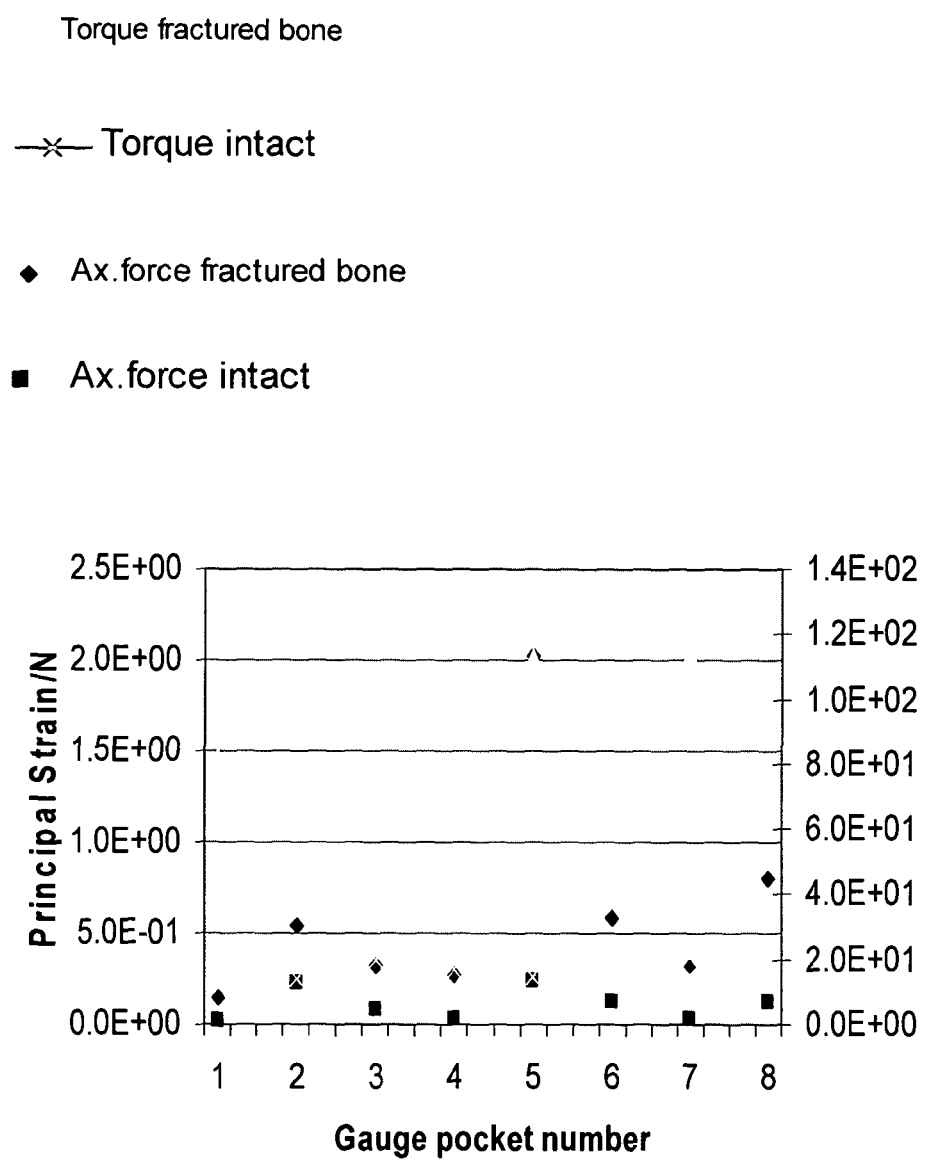
FIG. 12: Principal strain magnitude in relation to axial force and torque
Figure 13:
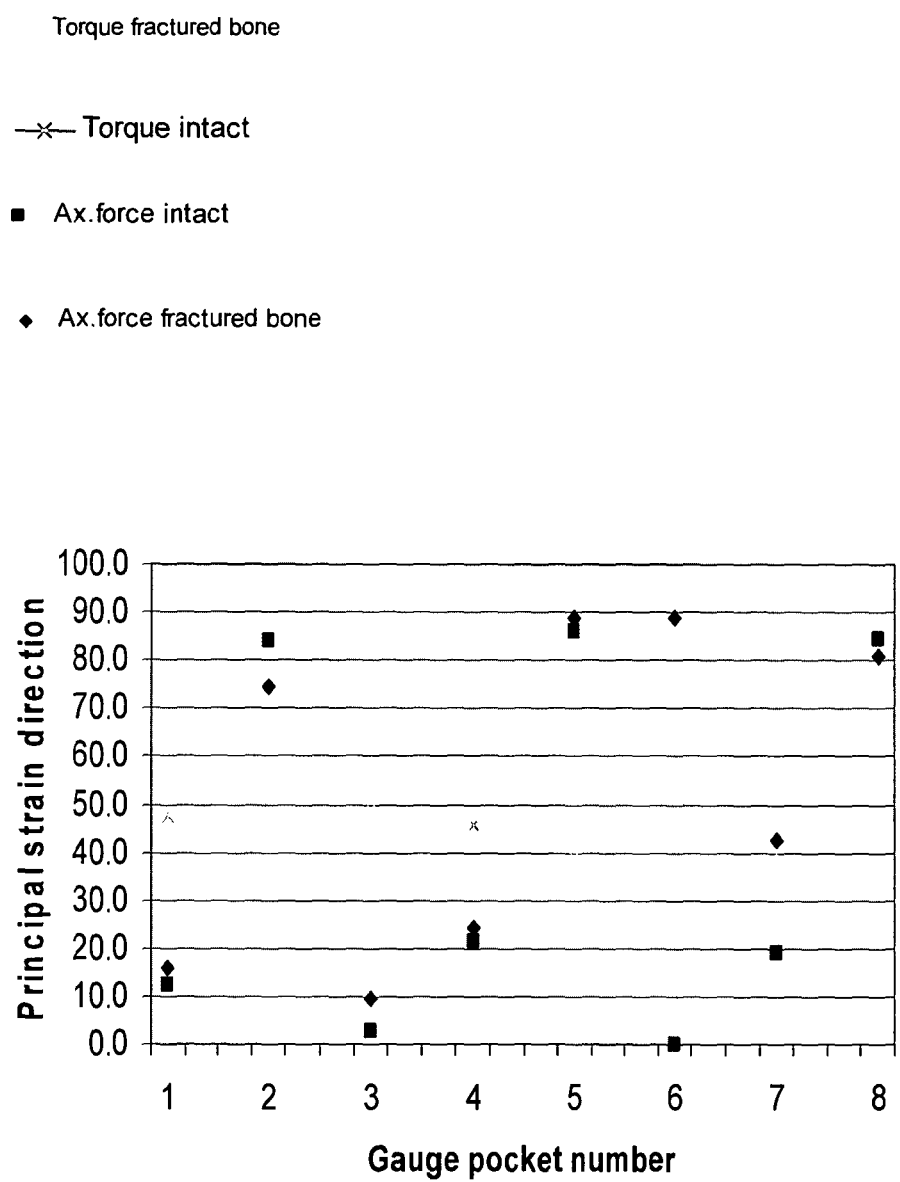
FIG. 13: Principal strain direction in relation to axial force and torque

FIGS. 12 and 13 demonstrates the strain magnitude and direction of principal strain for a mid-shaft fracture (42-C2) under axial force and torque. Several key concepts:
(i) there is a large change in magnitude of strain for both torque and axial force. This change is larger nearer the fracture site detected by gauges in pockets 5 and 6.
(ii) fracture effects torsion to a greater extent than axial strain.
(iii) the principal direction of strain does not appear to change very much, except for the axial load detected by gauges in pockets 6 and 7.

Figure 14:
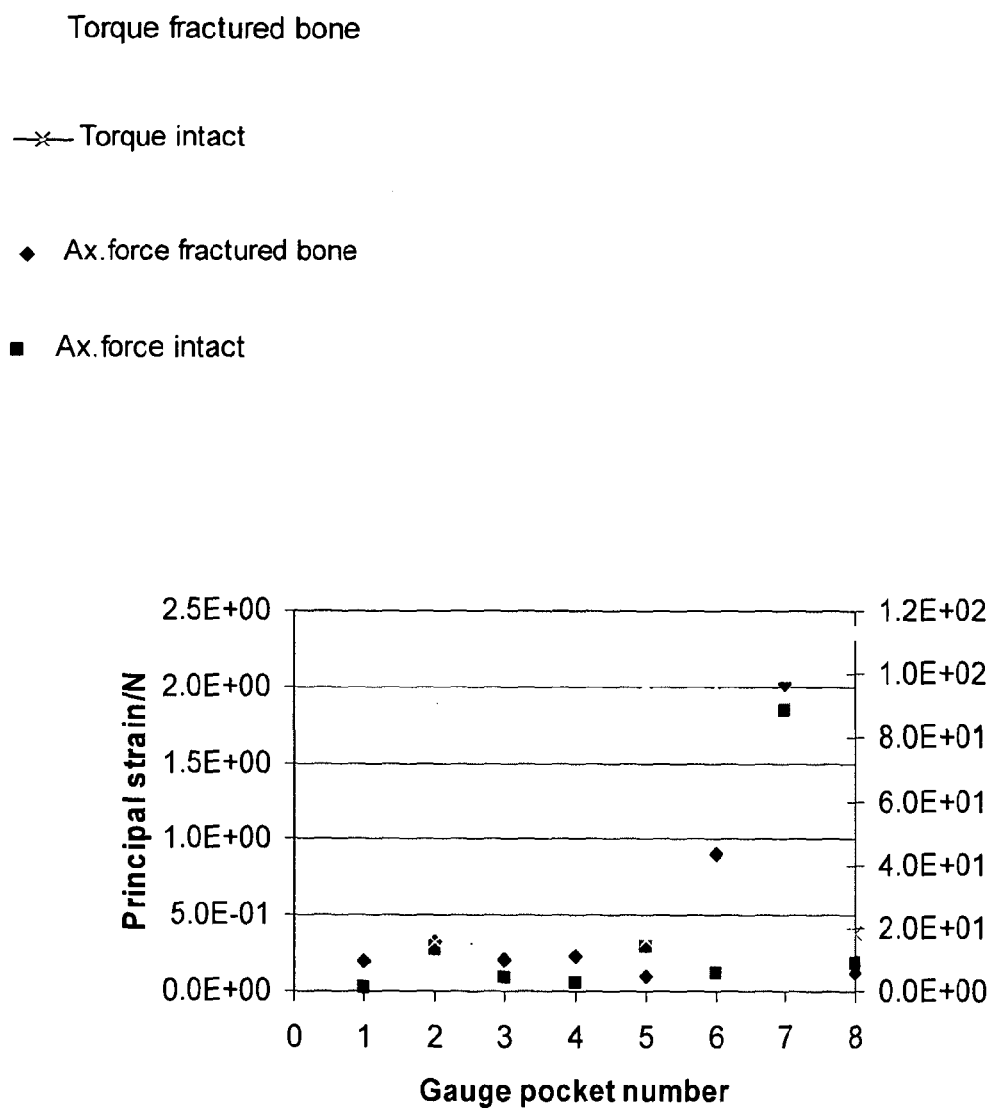
FIG. 14: Principal strain magnitude in relation to axial force and torque
Figure 15:
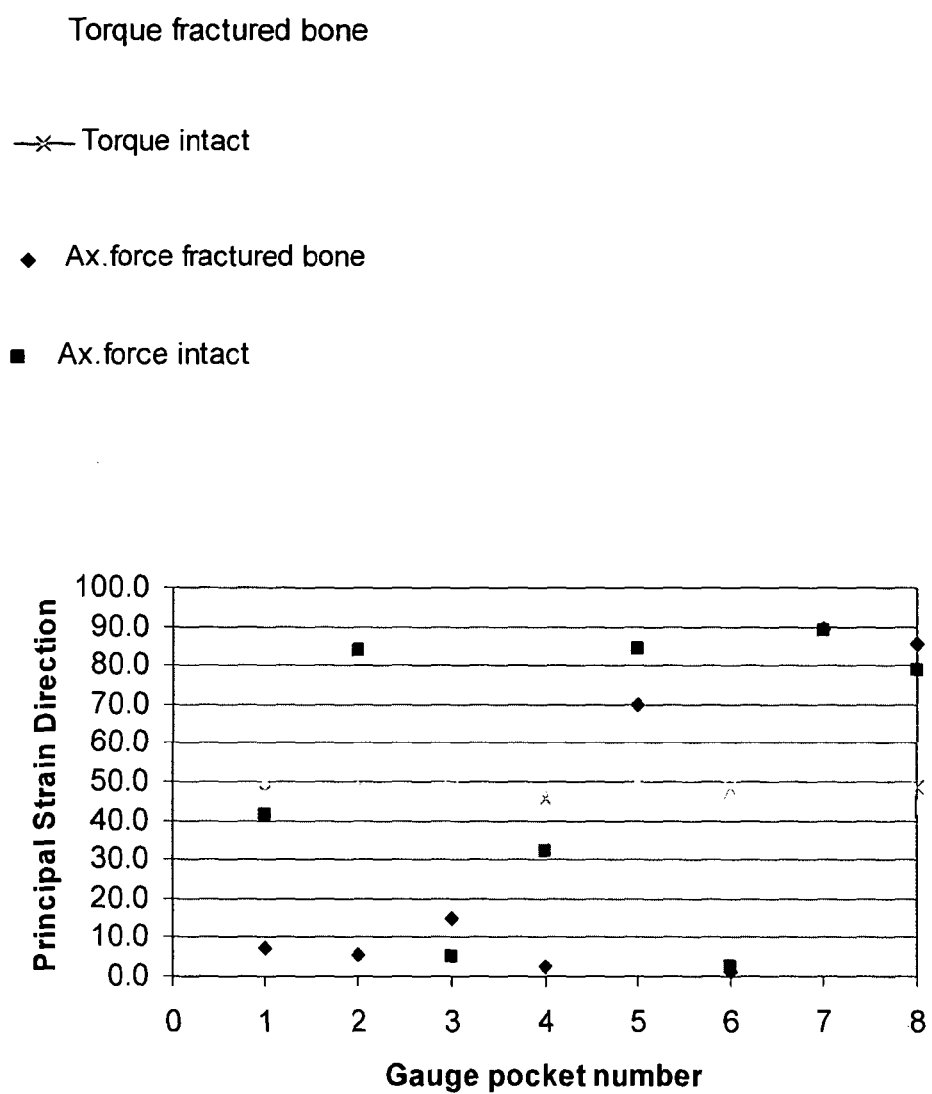
FIG. 15: Principal strain direction in relation to axial force and torque

FIGS. 14 and 15 demonstrates the strain magnitude and direction of principal strain for a distal fracture (AO 42-A3) under axial force and torque. Several key concepts:
(i) the magnitude of strain increased with distal compared to midshaft fracture
(ii) the direction of principal strain is relatively unaffected with respect to torsional stress compared to axial force application.
(iii) the direction of strain is more in line with gauge B, in the fractured bone; indicating a change in strain direction to be in line with the longitudinal axis of the nail.

Measurement of Inter-Fragmentary Movement in an IM Nail Under Axial and Torsional Loads Using RSA Precision and Accuracy Measurements of Inter-Fragmentary Movements.

When analyzing the radiographs it was possible to view all the tantalum markers inserted into the Sawbones®. Accuracy and precision calculations were performed because the difference between the migration measured with UmRSA®Software and the "gold standard" micrometer was not zero.

The tantalum beads were inserted into each segment of the Sawbones® in a random manner, and their relative placement within each segment was quantified by a measurement known as the "condition number". The condition number changes according to the arrangement of tantalum beads, with a low number indicating good marker scatter, and a high number suggesting that the markers are arranged in a more linear fashion.

The mean error of rigid body fitting (ME) values for linear displacement varied between 2 μm to 21 μm for the proximal fragment and from 4 μm to 18 μm for the distal segment. These values were similar to those seen in angular movement, which ranged from 2 μm to 12 μm for the proximal segment and from 5 μm to 20 μm for the distal segment. For y axis rotation, the ME values for the proximal segment were spread between 2 μm and 15 μm, and those in the distal segment varied between 6 μm and 15 μm.

In the situations of angular motion and y axis rotation, the condition number increased as the number of tantalum beads used to calculate precision was reduced from eight to three. For y rotation, the precision decreased by 1.46 fold when measured with three markers (0.145°) than with eight markers (0.099°). In angular movement, precision was 9.5-fold worse when calculated using three markers (0.095°) rather than eight (0.01°).

The precision of linear movement in the x, y and z planes also presented increasing condition numbers as the marker quantity decreased. The best precision for linear displacement was for y axis movement calculated with eight markers (±10.7 μm), and the worst was for z axis motion measured using eight markers (±144.7 μm). For x and y axis linear displacement, the number of markers and the condition number seemed to have little impact on the precision.

For y axis rotation, the mean of the prediction interval, that is to say the accuracy of the RSA measurements, varied between from ±0.04° to ±0.136° ($R^2 \geq 0.99851$, p<0.0005). Angular motion had accuracy ranging between ±0.036° degrees and ±0.04° ($R^2 \leq 1$, p<0.0005). In both types of movement, the worst accuracy was measured when only three tantalum beads were being used for the calculations. In the case of y axis rotation, decreasing the number of markers from 8 to 3, or increasing the condition number, decreased the accuracy by 3.3-fold.

The accuracy for linear displacement ranged from ±4.46 μm to ±60.3 μm ($R^2 \geq 0.96251$, p<0.0005). The best accuracy for translational movement was in the y axis and the worst was in the z-axis. In the x and y axes, the quantity of tantalum markers and their degree of scatter seemed to have little effect on the accuracy value.

Inter-Fragmentary Translations/Micromotion Measurements

Figure 16:
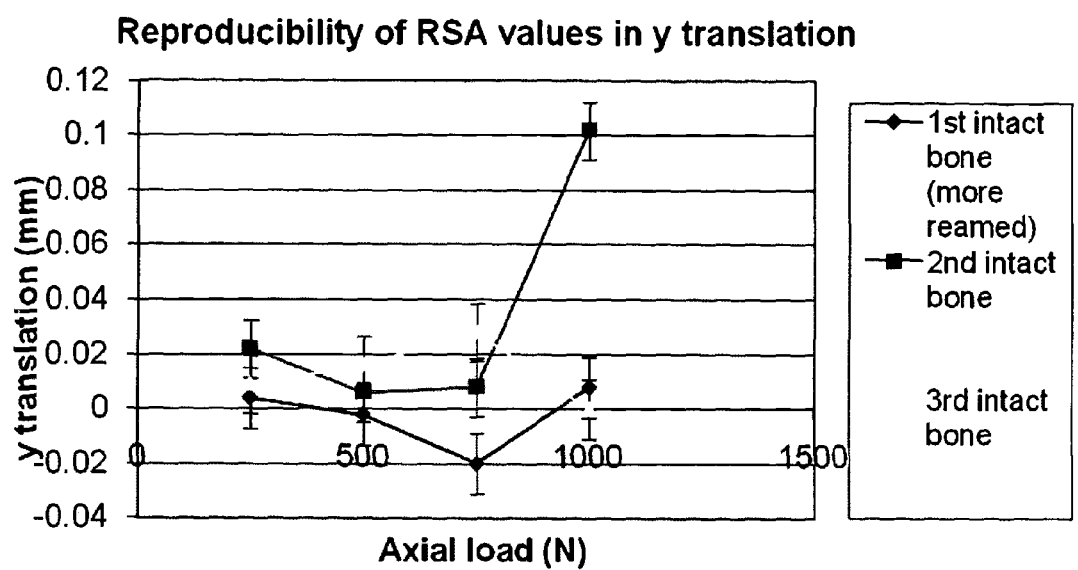
FIG. 16: Illustrates the Y axis translation (micromotion) of a distal segment relative to a proximal segment in intact bone

FIG. 16 illustrates the Y axis translation (micromotion) of a distal segment relative to a proximal segment in an intact bone.

Figure 17:
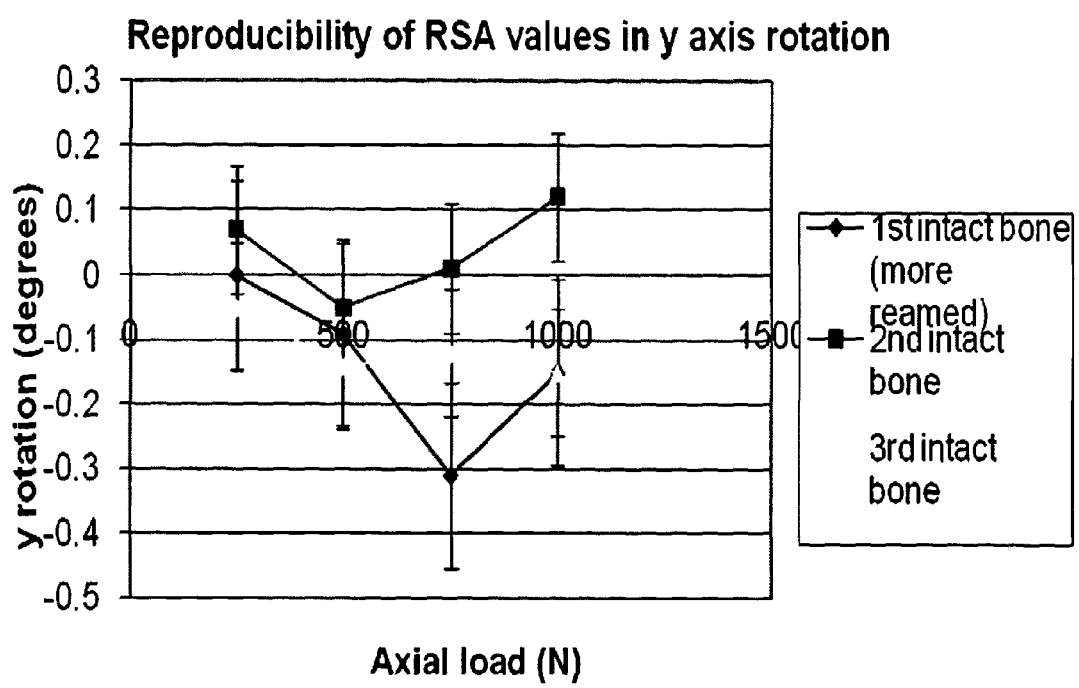
FIG. 17: Illustrates the Y axis rotation of a distal segment relative to a proximal segment in intact bone

FIG. 17 illustrates the Y axis rotation of a distal segment relative to a proximal segment in an intact bone.

Figure 18:
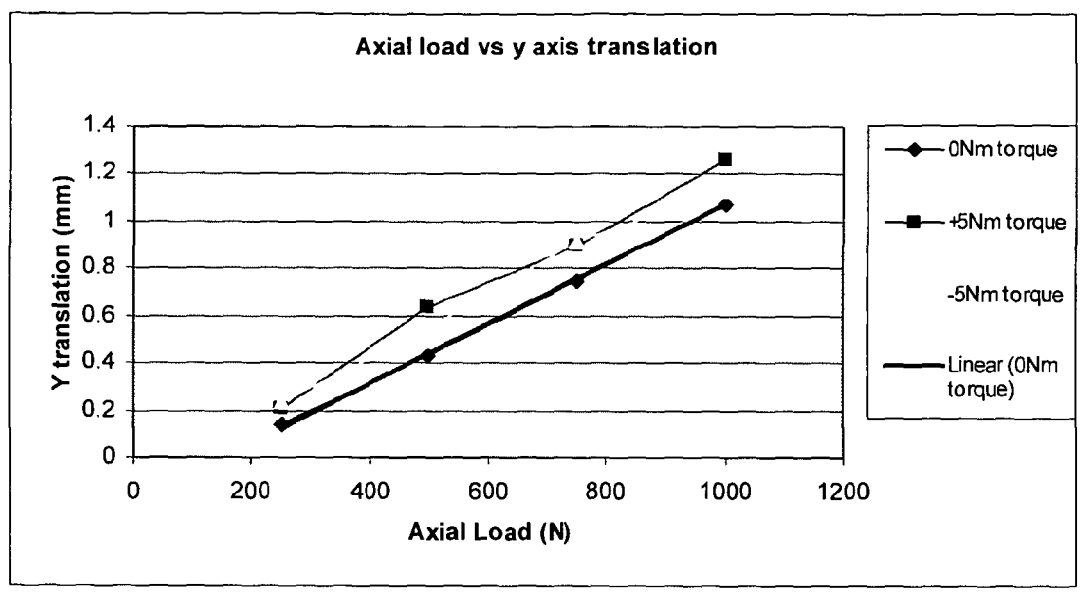
FIG. 18: illustrates the Y axis translation (micromotion) of a distal segment relative to a proximal segment in an AO 43-A3 fracture.

FIG. 18 illustrates the Y axis translation (micromotion) of a distal segment relative to a proximal segment in an AO 43-A3 fracture.

Figure 19:
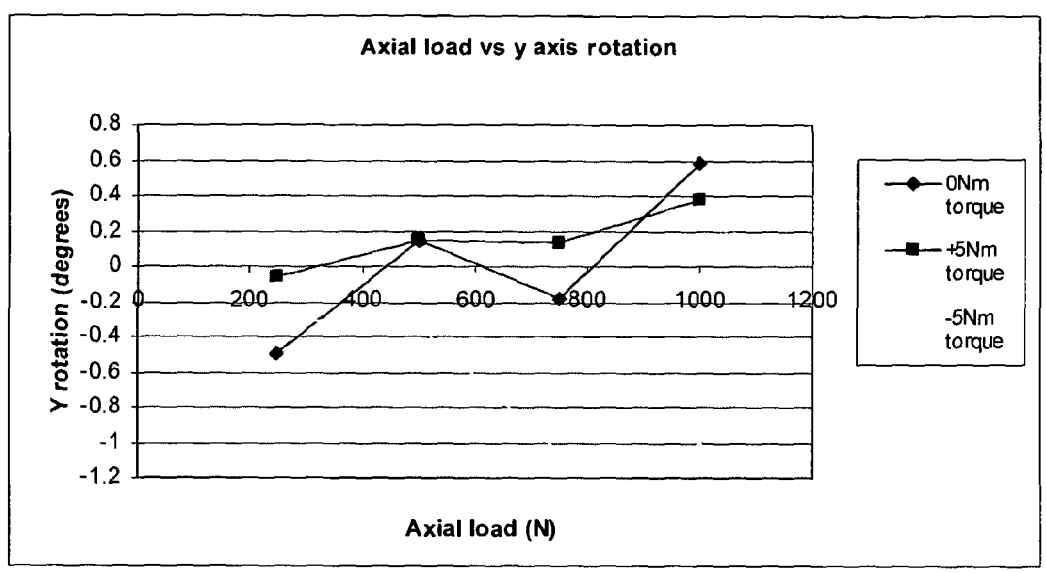
FIG. 19: illustrates the Y axis rotation of a distal segment relative to a proximal segment in an AO 43-A3 fracture.

FIG. 19 illustrates the Y axis rotation of a distal segment relative to a proximal segment in an AO 43-A3 fracture.

Figure 20:
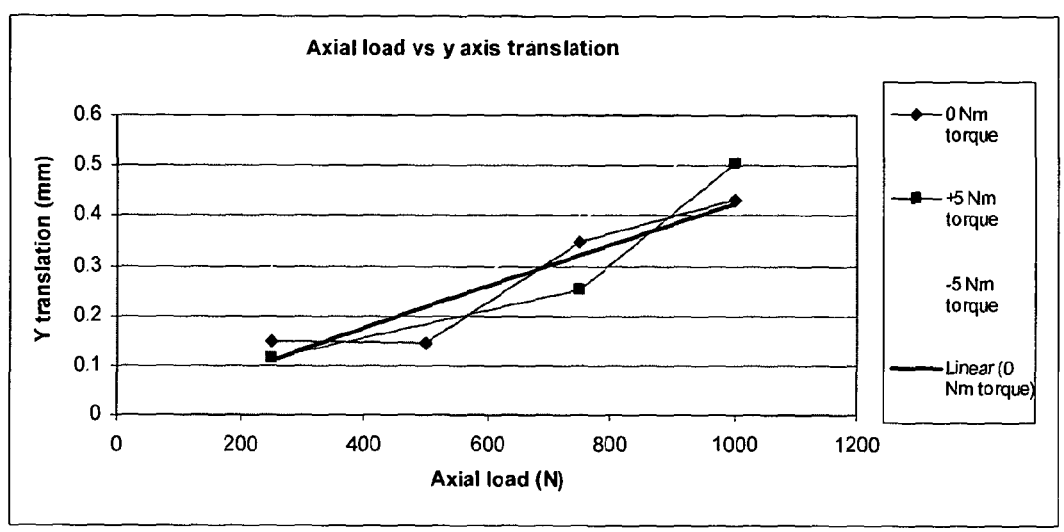
FIG. 20 illustrates the Y axis translation (micromotion) of a distal segment relative to a proximal segment in an AO 42-C2 fracture.

FIG. 20 illustrates the Y axis translation (micromotion) of a distal segment relative to a proximal segment in an AO 42-C2 fracture.

Figure 21:
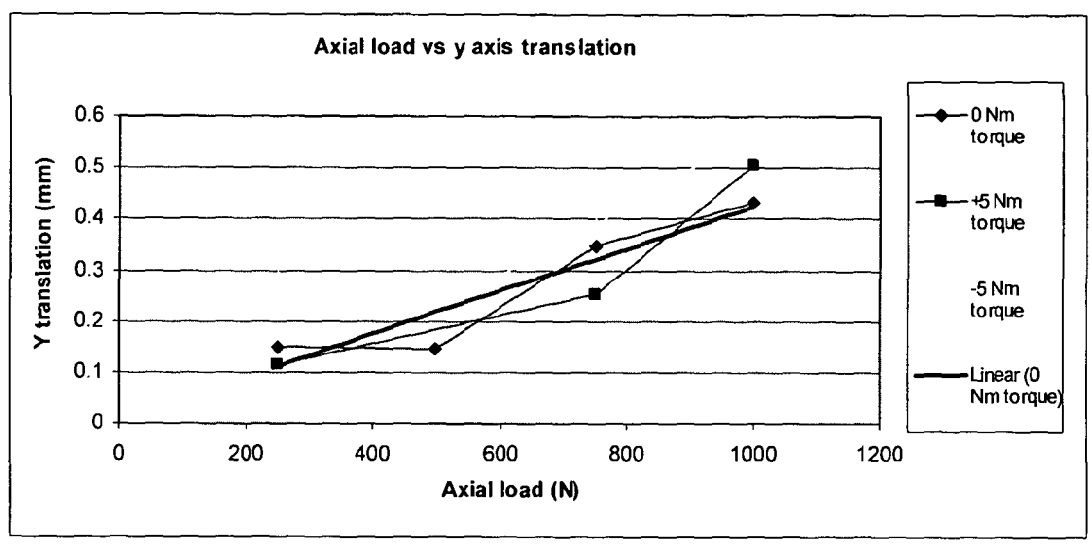
FIG. 21 illustrates the Y axis rotation of a distal segment relative to a proximal segment in an AO 42-C2 fracture.

FIG. 21 illustrates the Y axis rotation of a distal segment relative to a proximal segment in an AO 42-C2 fracture.

Figure 22:
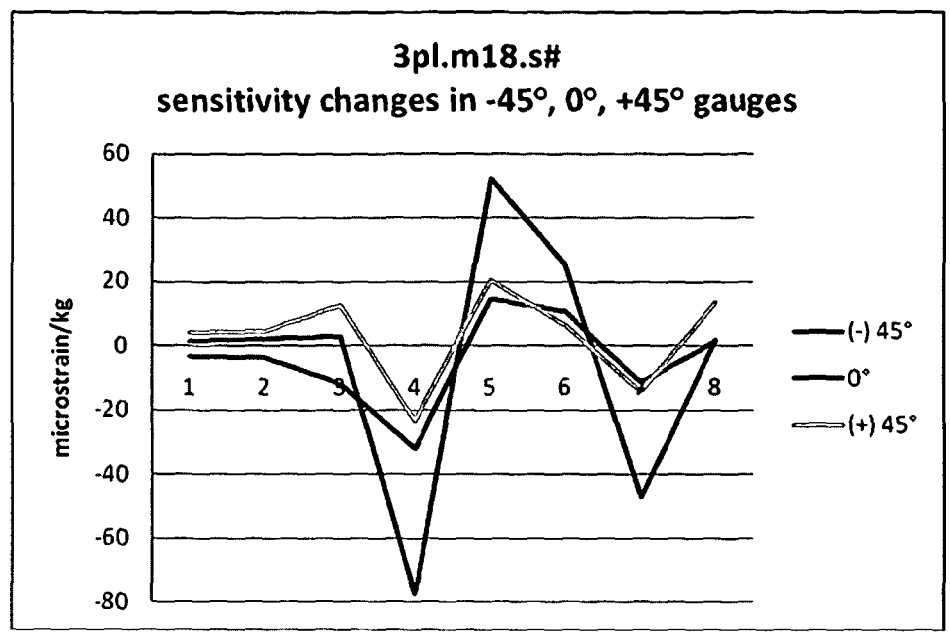
FIG. 22: sensitivity (microstrain/kg) plotted against strain gauge pocket number, illustrating the relationship in a segmental fracture with the loading moment being applied halfway at 18 cm between the two tibial suspension points

3. Measurement of Strain in Relation to 3-Point Loading in an IM Nail in a Tibial Fracture Testing the effect of different fracture configurations (AO: 42-A3, 42-C2, 43-A1, Non-Fractured Sawbone®) on the Sensitivity of the Strain Gauges When interpreting the results and graphs it is imperative to note the position of the fracture relative to the strain gauge pocket. This relationship is as follows:
1. Reduced AO 42-A3 simple transverse fracture—overlies pocket 6 (pockets 5 and 7 are adjacent)
2. Non-reduced transverse fracture AO 43-A1—overlies pocket 8
3. Non-reduced segmental fracture AO 42-C2—overlies pockets 4, 5 and 6 with the proximal and distal fracture lines overlying pockets 4 and 6 respectively FIG. 22 showing sensitivity (microstrain/kg) plotted against strain gauge pocket number, illustrates the relationship in a segmental fracture with the loading moment being applied halfway at 18 cm between the two tibial suspension points (the distance between the proximal and distal tibial suspension points=36 cm). In this unreduced fracture configuration the proximal and distal fracture lines overly pockets 4 and 6 respectively with the fracture segment overlying pocket 5. The greatest changes in sensitivity (microstrain/kg) from baseline are seen in the 0° gauges. In these gauges, the greatest deflections occur over pockets 4—the proximal fracture line, pocket 5 which is under the segment and pocket 6 which lies under the distal fracture line. The moment in this case was applied at 18 cm which is between pockets 4 and 5. We can thus justify choosing the 0° gauges in each of the 8 pockets for measurements because in 3-point loading they show the greatest deflection from baseline.

FIGS. 23-26 plot sensitivity (microstrain/kg) against the location of the strain gauge pocket for the intact Sawbone® and three simulated Sawbone® fractures (AO 42-A3, 43-A1, 42-C1 respectively). On each of the plots representing a specific fracture, the five applied moments are also represented.

Figure 23:
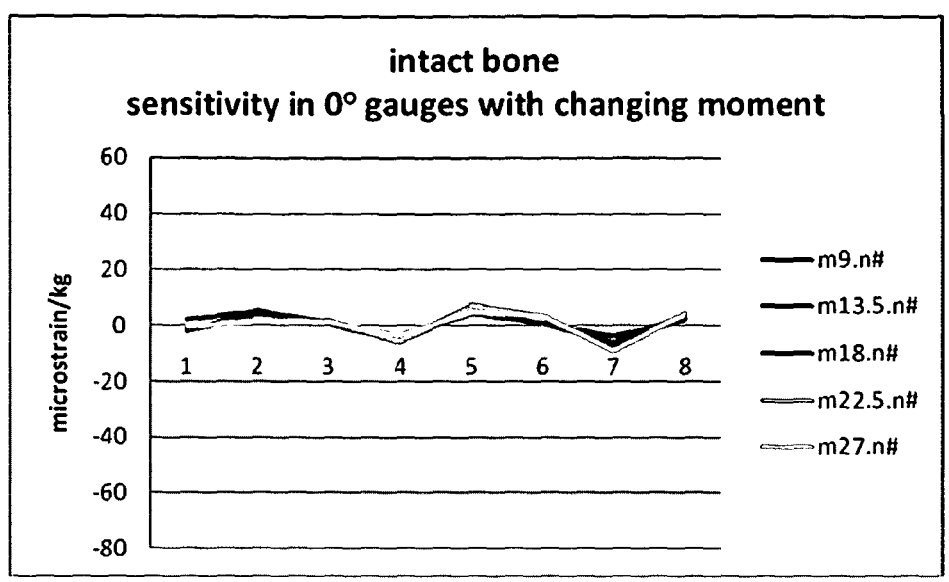
FIG. 23: illustrates the trace sensitivity against strain pocket

FIG. 23 shows the trace of sensitivity against strain gauge pocket for an intact Sawbone® 3 point-loaded at five separate positions. It demonstrates peak positive sensitivities occurring in the gauges under tension (pockets 2, 3, 5, 6 and 8). These are the medial and lateral pockets on the convex side of the nail. Negative peak sensitivities occur in pockets under compression (1, 4 and 7). These are the anterior pockets on the concave side of the nail. In the intact 38 cm tibia Sawbone® there appears to be a tri-modal distribution of positive sensitivity peaks at pockets 2, 5 and 8. These correspond to the lateral pockets. The lesser sensitivity in the medial pockets could as a result of rotation of the nail onto its lateral surface during loading. We can also observe that the sensitivity of a pocket is increased if the load is applied over it. Since no fracture is present, we would have expected all 8 strain gauge pockets to be equally sensitive, their sensitivity only being affected by position of moment application. Therefore we would have expected a symmetrical graph with similar peak sensitivities. The discrepancies in our graph are explained by the fact that the more sensitive gauges are closer to the point of moment application.

Figure 24:
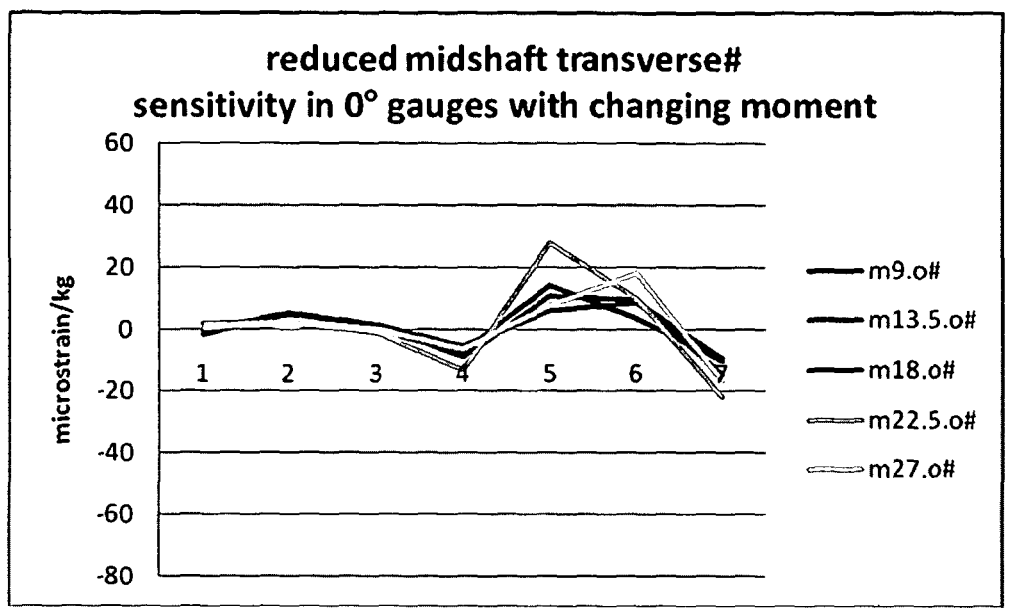
FIG. 24: illustrates an AO 42-A3 fracture which overlies pocket 6

FIG. 24 illustrates an AO 42-A3 fracture which overlies pocket 6 (pockets 5 and 7 are adjacent) The pockets closest to the fracture site are also the most sensitive in this fracture configuration. Sensitivity is maximised by applying the moment over the pocket under the fracture site, in this case at 22.5 cm.

Figure 25:
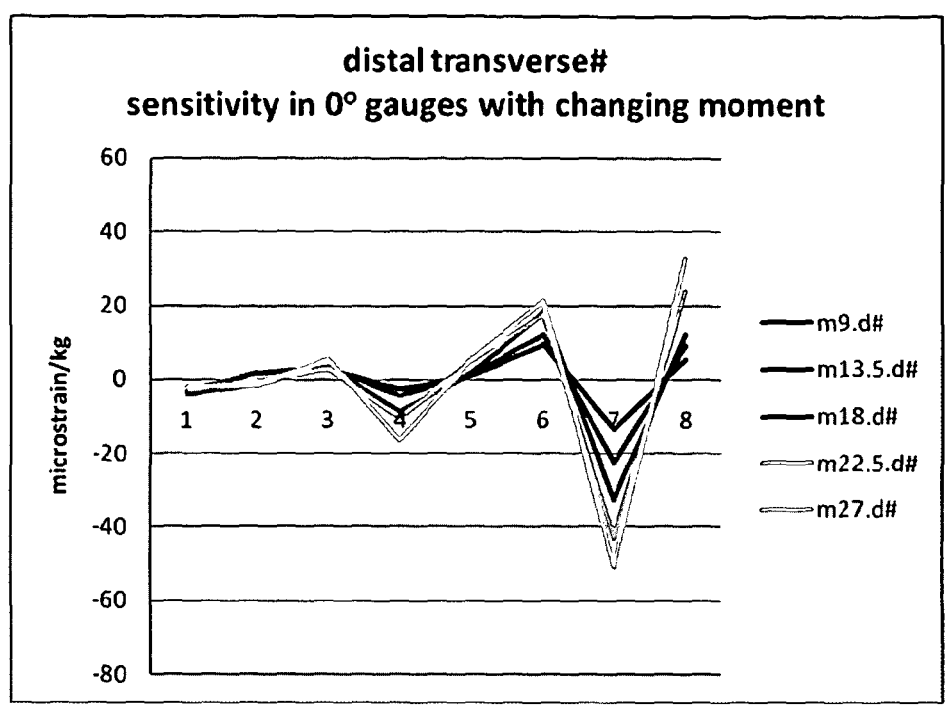
FIG. 25: illustrates an AO 43-A1 fracture which overlies pockets 7-8.

FIG. 25 illustrates an AO 43-A1 fracture which overlies between pockets 7 & 8. Pocket 7 and 8 are the most sensitive with the moment at 27 cm maximising strain gauge sensitivity.

Figure 26:
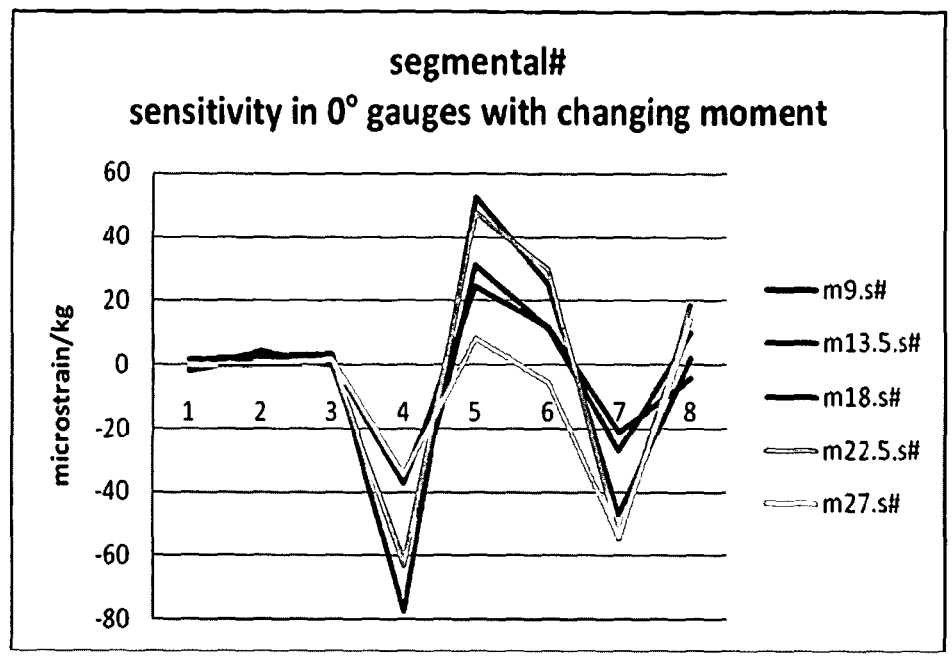
FIG. 26: illustrates an AO 42-C2 fracture which overlies pockets 4, 5 and 6 with the proximal and distal fracture lines overlying pockets 4 and 6 respectively

FIG. 26 illustrates an AO 42-C2 fracture which overlies pockets 4, 5 and 6 with the proximal and distal fracture lines overlying pockets 4 and 6 respectively. In this segmental fracture the pattern repeats. Pockets 4 and 5 show the greatest deflections. We would have however expected pocket 6 to show a greater deflection then pocket 7.

From FIGS. 23-26 the following is observed:
1) In the case of the three fractures configurations subjected to 3-point loading, the greatest sensitivity is achieved in the strain gauges closest to the fracture site.
2) Applying the bending moment over the fracture site maximises the sensitivity of the underlying strain gauges by up to 300 strain counts/kg (in fracture AO 42-C2)
3) The strain gauges become less sensitive as the nail-bone composite stiffens, as demonstrated by the non-fractured and reduced Sawbones®.
4) In the non-fractured Sawbone®, consistently with the findings in the fractured Sawbones®, applying the bending moment over the strain gauge pocket increases its sensitivity. All 8 strain gauge pockets appear approximately equally sensitive.

Inter-Fragmentary Movement in Response to Three-Point Loading

There were two purposes for utilising the RSA methodology. The first purpose of the RSA was to act as a control to the strain count versus load (Kg) measurements. The second purpose was to enable a relationship to be established between applied bending moment and bending at the fracture site.

These results to showed that the simulated "callus" stiffness was physiologically representative Rotation in the Z plane was chosen to measure bending of the bone.

Figure 27:
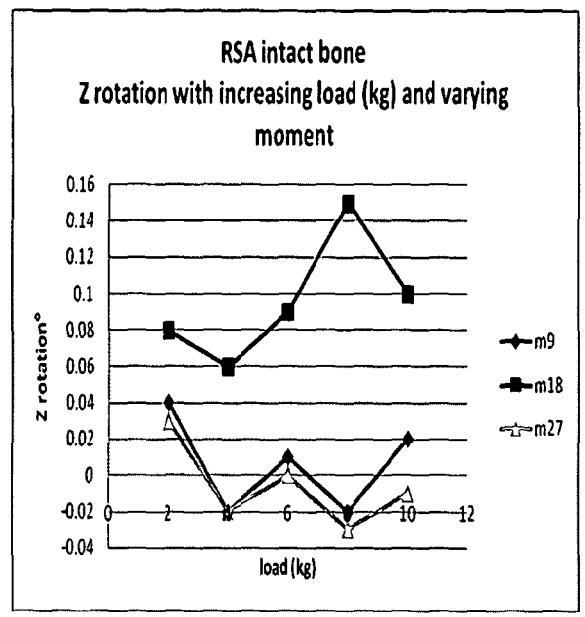
FIG. 27: RSA trace illustrating increasing Z rotation with increasing load
Figure 27:
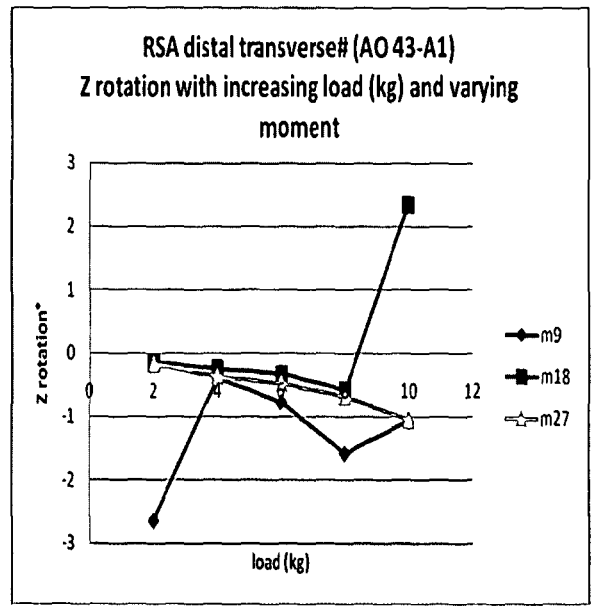
Figure 27:
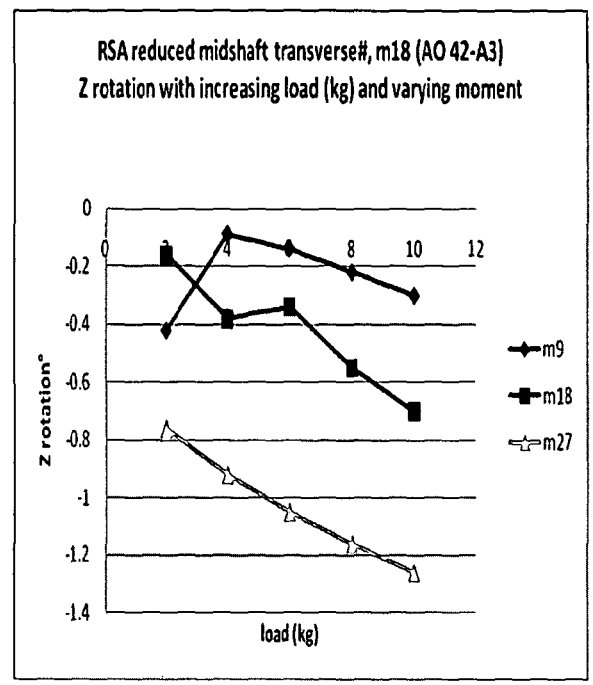
Figure 27:
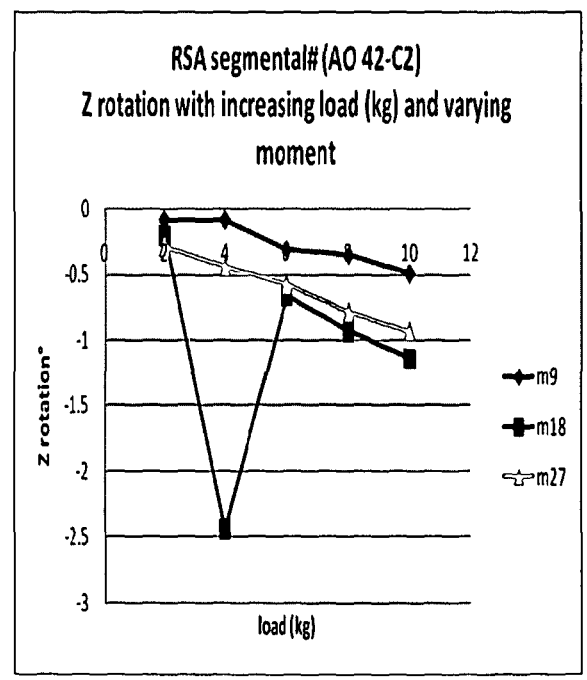

The results (FIG. 27) show that there is increasing Z rotation with increasing load. This corroborates the strain count readings which also increase (if under tension, and decrease when under compression) with increasing load.

Detecting Changes in Stiffness of the Sawbones® with the Instrumented Nail (Callus Simulation)

Figure 28:
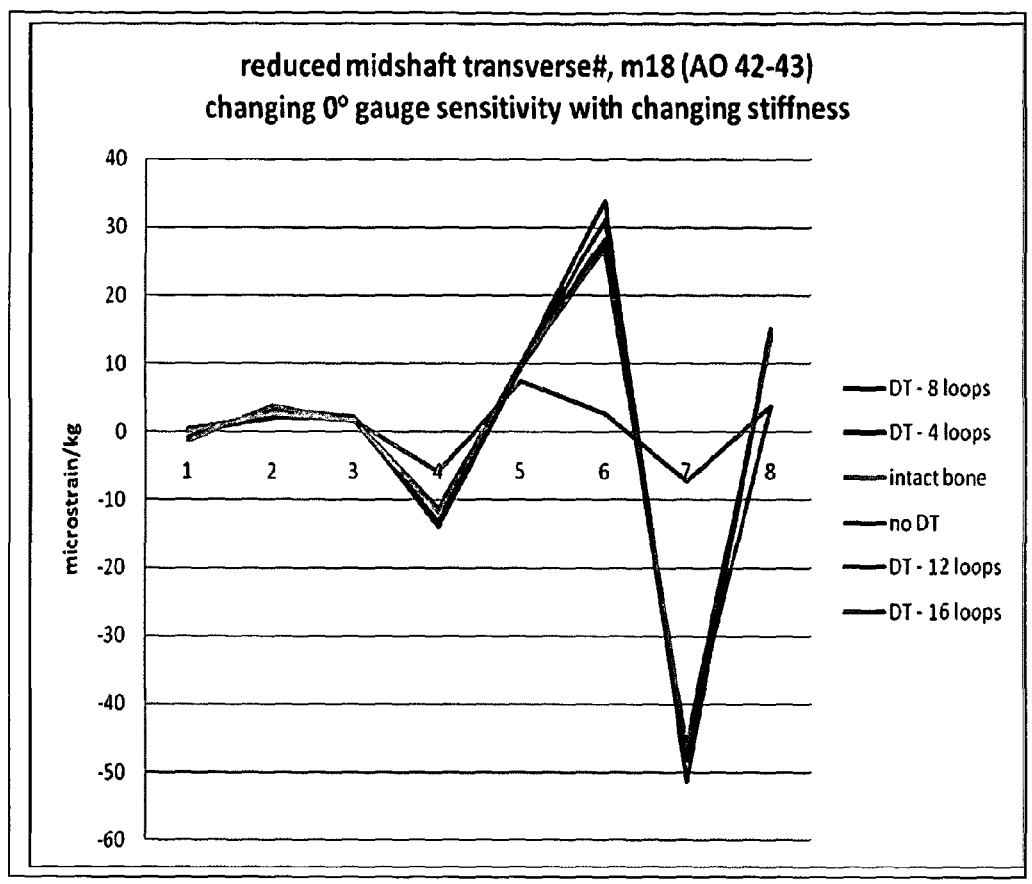
FIG. 28: RSA trace of sensitivity against strain pocket with incrementally increasing stiffness of the nail-bone composite

FIG. 28 is a trace of sensitivity against strain gauge pocket with incrementally increasing stiffness of the nail-bone composite. The stiffer the composite the smaller the peak sensitivity. (Key: DT=reinforced polyethylene tape, the number refers to the number of loops of reinforced polyethylene tape).

This graph prooves the concept that the instrumented nail is able to detect changes in stiffness. This ability is an imperative property of the instrumented nail if it is to fulfil its ultimate role of being able to detect delayed or non-union on the basis of changing nail-bone composite stiffness over time.

In order to quantify the stiffness of the reinforced polyethylene tape "callus" simulation, RSA was performed on DT-4 loops and DT-8 loops models.

Figure 29:
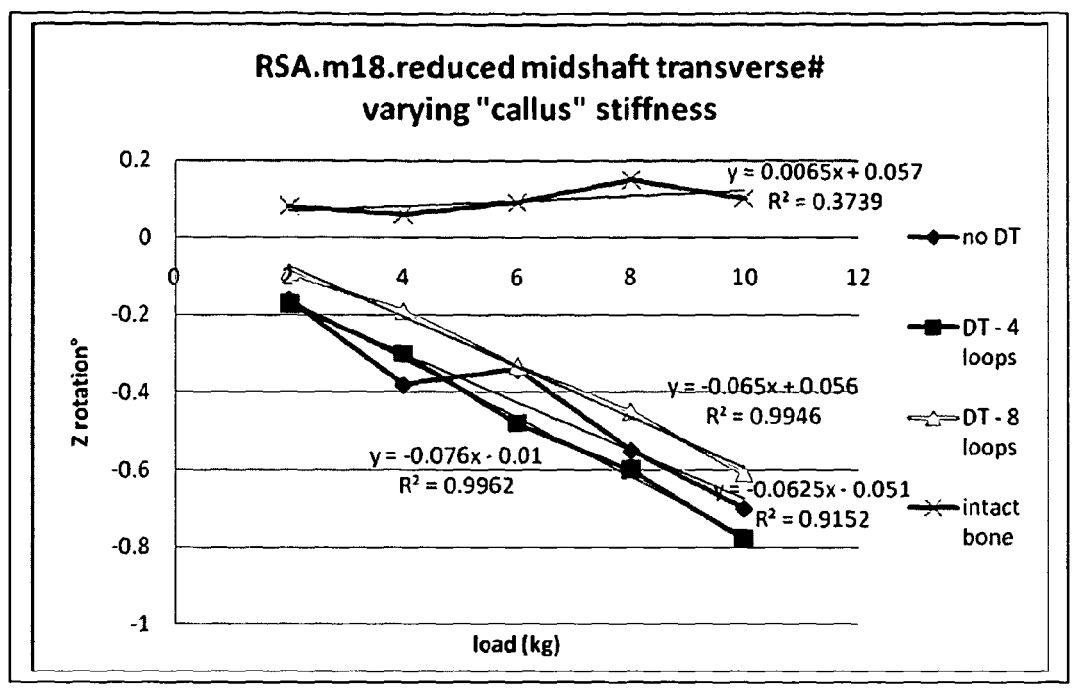
FIG. 29: RSA trace of rotation in the Z plane against load for 4 and 8 loop reinforced polyethylene tape "callus"

RSA traces (FIG. 29) of rotation in the Z plane against load for the 4 and 8 loop reinforced polyethylene tape "callus" models enabled the quantification of the stiffness by calculating the reciprocal value of the gradient.

The stiffness of the simulated "callus" nail-bone composite was calculated as follows:

For DT-4 loops Z rotation gradient=−0.076 degrees/kg, therefore stiffness=1/gradient=13.15 kg/°=131.5 N/°. At moment 18 cm=23.6 Nm/°.

For DT-8 loops Z rotation gradient=−0.065 degrees/kg, therefore stiffness=1/gradient=15.4 kg/°=154N/°. At moment moment 18 cm, stiffness=27.7 Nm/°.

The gradient of the fracture without any reinforced polyethylene tape indicates a greater stiffness than for DT-4 and DT-8. However the correlation between the two variables is also lower in this case. This may suggest that this is an abherent result.

The stiffness in the sagittal plane of the "callus" simulated by four and eight loops of reinforced polyethylene tape equalled 23.6 Nm/° and 27.7 Nm/° respectively. The eight loop "callus" was stiffer as one would expect, requiring a greater moment to produce one degree of rotation. Both simulations were approximately within the physiological range of human bone callus stiffness. From the work of Richardson et al. the callus at the point of tibial union can be considered to have a stiffness of 15 Nm/° in the sagittal plane.

The instrumented nail is able to detect differences in stiffness of at least 27.7−23.6=4.1 Nm/°. Thus the nail has sufficient resolution to be able to detect physiologically relevant stiffness changes. Ultimately, the nail has to be sensitive enough to be able to detect stiffness changes in the first one month of callus formation.

4. Correlation of strain with fracture type, fracture location, Callus Maturation, Applied Load and Position of Strain Gauges.

Figure 32:
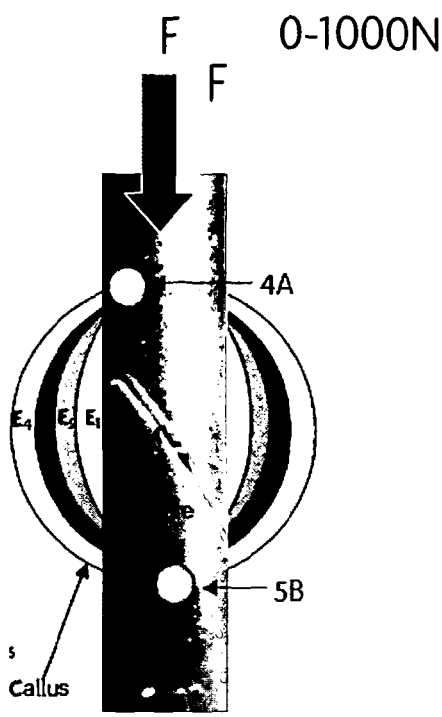
FIG. 32: Fracture model: 42-A2-A0; pocket/gauge: 4A; 5B. stance-Off-axis compression loading
Figure 32:
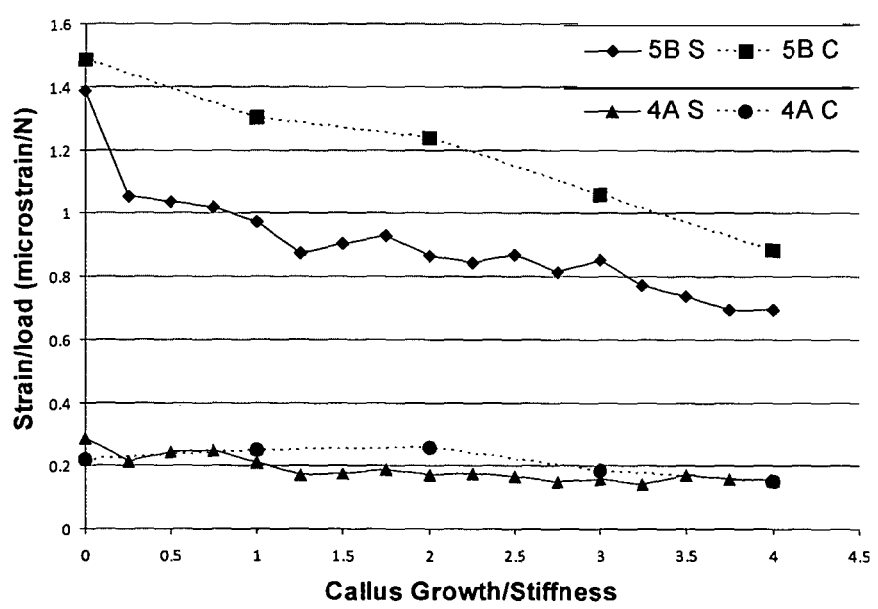

FIG. 32
Fracture Model:
Reduced Fracture 42-A2-AO
Loading pattern: stance "off-axis axial compression loading" during 4-6 weeks of simulated healing
Gauges located either side of the fracture site in pocket 4 (gauge orientation A=45°) and pocket 5 (gauge orientation B=0°)
S=Segmental application of the callus; C=Circumferential application of the callus
Conclusion:
Gauge B in pocket 5, located distal of the fracture site, is capable of sensing callus growth/stiffness increase over time in both models of callus formation.
Gauge A in pocket 4, located proximal to the fracture site, is not sensitive enough to sense any callus growth/stiffness increase over time in either model of callus formation under off-axis axial compression loading.

Figure 33:
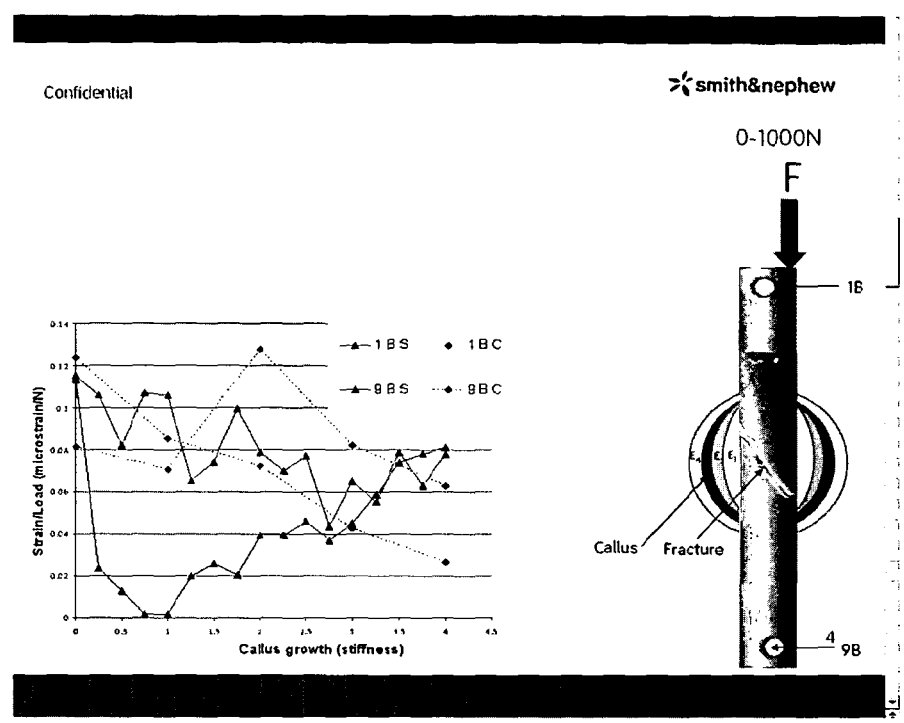
FIG. 33: Fracture model: 42-A2-A0; pocket/gauge: 1B; 9B. stance-Off-axis compression loading

FIG. 33
Fracture Model:
Reduced fracture 42-A2-AO
Loading pattern: stance "off-axis axial compression loading" during 4-6 weeks of simulated healing
Gauges located at distal and proximal ends of nail in pocket 1 (gauge orientation B=0°) and pocket 9 (gauge orientation B=0°)
S=Segmental application of the callus; C=Circumferential application of the callus
Conclusion:
Although Gauge B in pocket 9, located at the distal end of the nail, is capable of sensing callus growth/stiffness increase over time in the model of callus formation in which the callus was circumferentially applied, this gauge is not as sensitive as the gauge in pocket 5 (see FIG. 32). Additionally, this gauge is not capable of sensing callus growth/stiffness increase over time in the model of callus formation in which the callus was segmentally applied and hence this gauge is not considered as clinically useful for determining fracture healing for this type of fracture pattern.
Gauge B in pocket 1 is not sensitive enough to sense any callus growth/stiffness increase over time in either model of callus formation.

Figure 34:
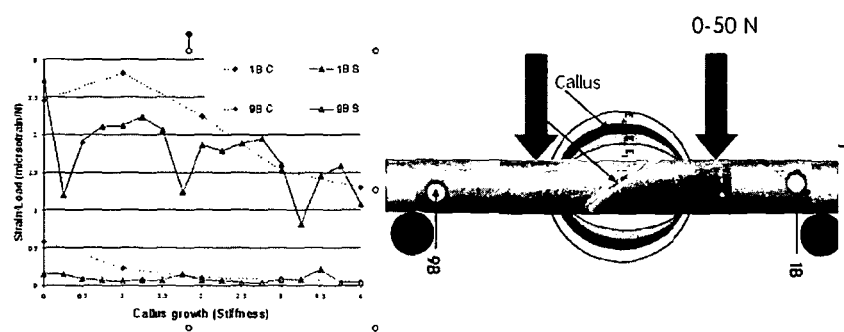
FIG. 34: Fracture model: 42-A2-A0; pocket/gauge: 1B; 98. stance-4 point bending

FIG. 34
Fracture Model:
Reduced fracture 42-A2-AO
Loading pattern: supine "4 point bending loading" during 4-6 weeks of simulated healing
Gauges located at distal and proximal ends of nail in pocket 1 (gauge orientation B=0°) and pocket 9 (gauge orientation B=0°)
S=Segmental application of the callus; C=Circumferential application of the callus
Conclusion:
Gauge B in pocket 1 is capable of sensing callus growth/stiffness increase over time in the model of callus formation in which the callus was circumferentially applied.
Gauge B in pocket 1 is capable of sensing callus growth/stiffness increase over time in the models of callus formation in which the callus was segmentally applied, although there is significant amount of "noise".
Gauge B in pocket 9 is not sensitive enough to sense any callus growth/stiffness increase over time in either model of callus formation, this could be as a result of contact of the distal section of the nail with the walls of the intramedullary canal, which can lead to interference in strain measurements.

Figure 35:
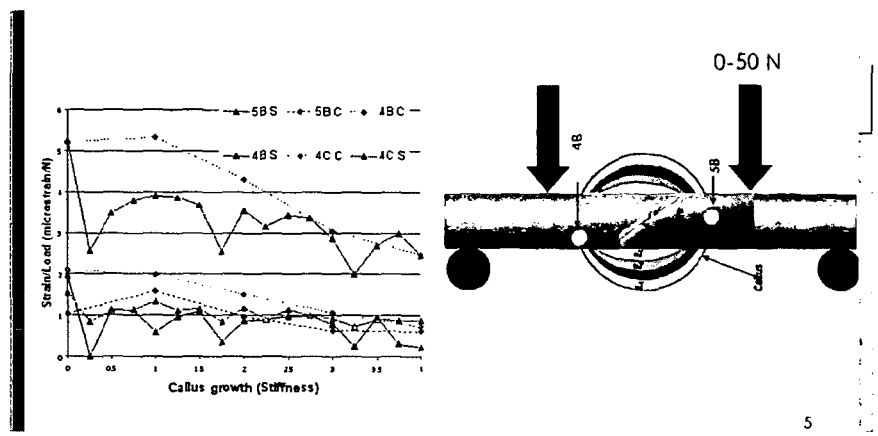
FIG. 35: Fracture model: 42-A2-A0; pocket/gauge: 4B; 5C. stance-4 point bending

FIG. 35
Fracture Model:
Reduced Fracture 42-A2-AO
Loading pattern: supine "4 point bending loading" during 4-6 weeks of simulated healing Gauges located either side of the fracture site in pocket 4 (gauge orientation B=0°) and pocket 5 (gauge orientation C=−45°)
S=Segmental application of the callus; C=Circumferential application of the callus
Conclusion:
Gauge B in pocket 4 is capable of sensing callus growth/stiffness increase over time in both models of callus formation.
Gauge B in pocket 5 and gauge C in pocket 4 is not sensitive enough to sense any callus growth/stiffness increase over time in either model of callus formation.

Figure 36:
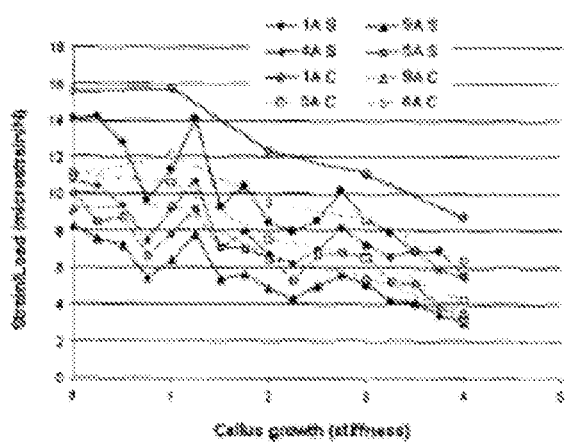
FIG. 36: Fracture model: 42-A2-A0; pocket/gauge: 1A; 4A; 5A; 9A. stance: torque loading
Figure 36:
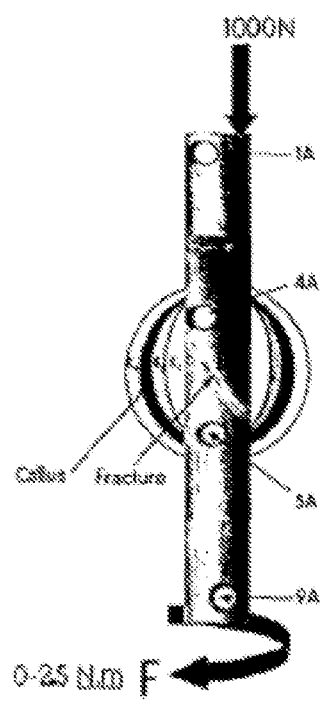
Figure 37:
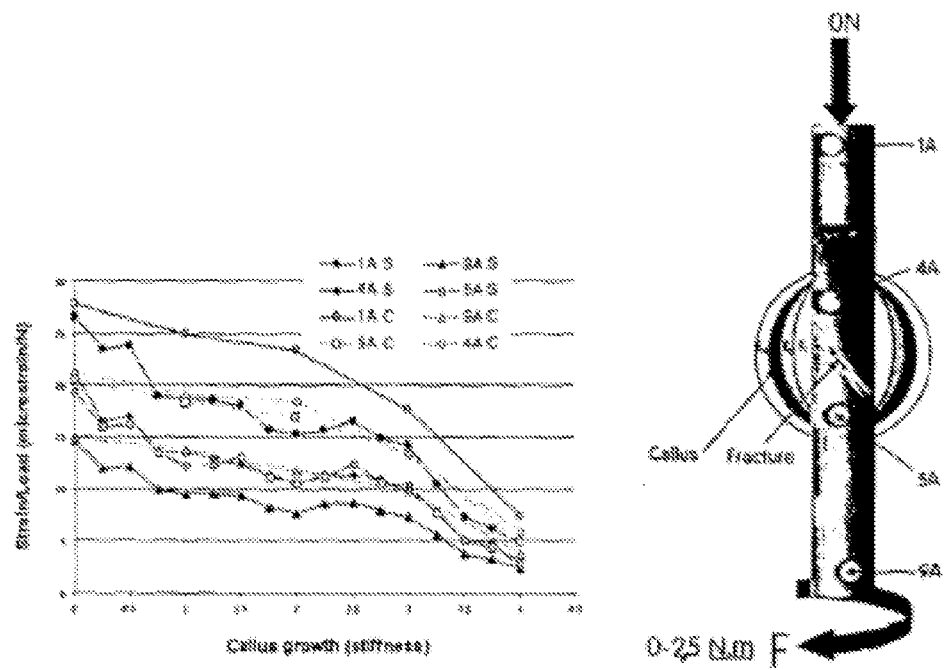
FIG. 37: Fracture model: 42-A2-A0; pocket/gauge: 1A; 4A; 5A; 9A. supine: torque loading
Figure 38:
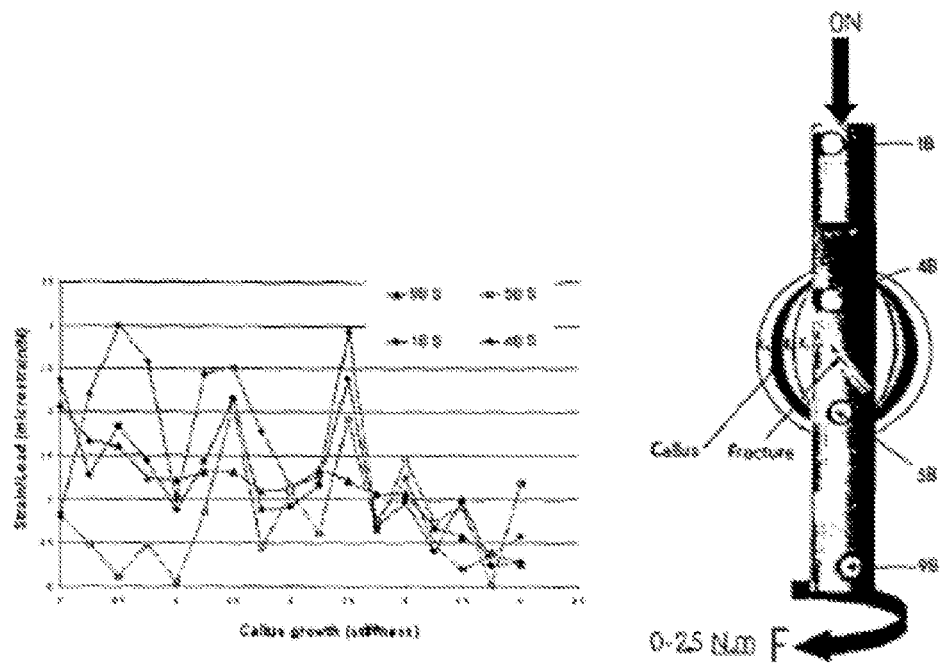
FIG. 38: Fracture model: 42-A2-A0; pocket/gauge: 1B; 4B; 5B; 9B. supine: torque loading

FIG. 36
Fracture Model:
Reduced Fracture 42-A2-AO
Loading pattern: stance "torque loading of 0-2.5N·m at 1000N compresion" during 4-6 weeks of simulated healing
Gauges located either at proximal and distal ends in pockets 1, 4, 5 and 9 (gauge orientation A=45°);
S=Segmental application of the callus; C=Circumferential application of the callus
Conclusion:
All of the A gauges, independent of location on the nail relative to the fracture site, are capable of satisfactorily sensing callus growth/stiffness increase over time in either model when torque loading is applied in the supine position.

FIG. 37

Fracture Model:

Reduced Fracture 42-A2-AO

Loading pattern: supine "torque loading of 0-2.5N·m at zero compression load" during 4-6 weeks of simulated healing Gauges located either at proximal and distal ends in pockets 1, 4, 5 and 9 (gauge orientation A=45°);

S =Segmental application of the callus; C=Circumferential application of the callus Conclusion:

Likewise all of the A gauges, independent of location on the nail relative to the fracture site, are capable of satisfactorily sensing callus growth/stiffness increase over time in either model when torque loading is applied in the supine position.

FIG. 38

Fracture Model:

Reduced Fracture 42-A2-AO

Loading pattern: supine "torque loading of 0-2.5N·m at zero compresion load" during 4-6 weeks of simulated healing Gauges located either at proximal and distal ends in pockets 1, 4, 5 and 9 (gauge orientation B=0°);

S=Segmental application of the callus; C=Circumferential application of the callus Conclusion:

None of the B gauges, are considered as satisfactory for sensing callus growth/stiffness increase over time in either model when torque loading is applied in the supine position.

Overall Conclusion:

Torque gauges especially at 45° (i.e gauge A and C) are able to detect a decrease in strain away from the fracture site but appear to be unable to determine site location.

Offset axial loading can detect site location from multiple gauge sites, but especially at 0° (i.e gauge B), but cannot detect changes in strain at fracture sites at distal location.

4 point bending can also detect changes in strain at remote locations but not as well as torque bending.

References

Bragdon, C. R., Malchau, H., Yuan, X., Perinchief, R., Karrholm, J., Borlin, N., Estok, D. M., & Harris, W. H. 2002, "Experimental assessment of precision and accuracy of radiostereometric analysis for the determination of polyethylene wear in a total hip replacement model", *J. Orthop. Res.*, vol. 20, no. 4, pp. 688-695.

Court-Brown 1995, "The epidemiology of tibial fractures", *Journal of Bone and Joint Surgery. British Volume*, vol. 77, no. 3, p. 417.

Grutter 2000, "The epidemiology of diaphyseal fractures of the tibia", Injury, vol. 31, p. 64.

Gustilo, R. B. & Anderson, J. T. 1976, "Prevention of infection in the treatment of one thousand and twenty-five open fractures of long bones: retrospective and prospective analyses", *Journal of Bone and Joint Surgery*, vol. 58, no. 4, pp. 453-458.

Hooper G J 1991, "Conservative management or closed nailing for tibial shaft fractures. A randomised prospective trial", *Journal of Bone and Joint Surgery. British Volume*, vol. 73, no. 1, p. 83.

Kanakaris, N. 2007, "The health economics of the treatment of long-bone non-unions", *Injury*, vol. 38, p. 77.

Lacroix, D and Prendergast P. J 2001, !A mechano-regulation model for tissue differentiation during fracture healing: analysis of gap size and loading". Journal of Biomechanics Vol. 35, Issue 9, Pages 1163-1171 (September 2002)

Littenberg, B. E. N. J., Weinstein, L. P., McCarren, M. A. D. E., Mead, T. H. O. M., Swiontkowski M. F., Rudicel, S. A., & Heck, D. A. V. I. 1998, "Closed Fractures of the Tibial Shaft. A META-analysis of Three Methods of Treatment", *Journal of Bone and Joint Surgery*, vol. 80, no. 2, pp. 174-183.

Madanat, R., Moritz, N., Larsson, S., & Aro, H. T. 2006, "RSA applications in monitoring of fracture healing in clinical trials", *Scand. J. Surg.*, vol. 95, no. 2, pp. 119-127.

Phieffer, L. S. & Goulet, J. A. 2006, "Delayed Unions of the Tibia", *Journal of Bone and Joint Surgery*, vol. 88, no. 1, pp. 205-216.

Schmidt et at 2003, "Treatment of Closed Tibial Fractures", *Journal of Bone and Joint Surgery*, vol. 85, no. 2, pp. 352-368.

Schneider, E., Michel, M. C., Genge, M., Zuber, K., Ganz, R., & Perren, S. M. 2001, "Loads acting in an intramedullary nail during fracture healing in the human femur", *J. Biomech.*, vol. 34, no. 7, pp. 849-857.

Valstar, E. R., Gill, R., Ryd, L., Flivik, G., Borlin, N., & Karrholm, J. 2005, "Guidelines for standardization of radiostereometry (RSA) of implants", *Acta Orthop.*, vol. 76, no. 4, pp. 563-572.

The invention claimed is:

1. A telemetric orthopaedic implant system, the system comprising:
   (a) an orthopaedic implant, the orthopaedic implant having a longitudinal axis and comprising:
      (i) a strain gauge orientated at about +45° or about −45° relative to the longitudinal axis of the implant;
      (ii) a recess adapted to receive said strain gauge(s);
      (iii) an electronic component electrically connected to at least a power supply, a first transmitter, a first receiver, and a first microprocessor;
      (iv) a recess adapted to receive said electronic component;
      (v) potting material to seal said recess(es);
      (vi) a power source electrically connected to said electronic component; and;
   (b) a control unit, the control unit comprising;
      (vii) a second microprocessor,
      (viii) a second transmitter electrically connected to said second microprocessor, the second transmitter adapted to send a signal to said first receiver of said electronic component; and
      (ix) a second receiver electrically connected to said second microprocessor, the second receiver adapted to receive data from said transmitter of said electronic component.

2. The telemetric orthopaedic implant system of claim 1, which comprises at least one further strain gauge orientated at about 0° or at about 90° relative to the longitudinal axis of the implant.

3. The telemetric orthopaedic implant system of claim 2, wherein at least one of the strain gauges are located at about +45°, at least one of the strain gauges are orientated at about −45° and a strain gauge orientated at about 0°.

4. The telemetric orthopaedic implant system of claim 1, wherein at least one of the strain gauges are orientated at about +45° and at least one of the strain gauges are orientated at about 0°, or at least one of the strain gauges are orientated at about +45° and a strain gauge orientated at about 90°, or at least one of the strain gauges are orientated at about −45° and a strain gauge orientated at about 0°, or at least one of the strain gauges are orientated at about −45° and a strain gauge orientated at about 90°.

5. The telemetric orthopaedic implant system of claim 1, wherein the recess for receiving the strain gauges and the electronic component is the same recess.

6. The telemetric orthopaedic implant system of claim 1, wherein there is a single recess.

7. The telemetric orthopaedic implant system of claim 6, wherein the single recess is located in the proximal portion of the telemetric orthopaedic implant.

8. The telemetric orthopaedic implant system of claim 1, wherein said orthopaedic implant is an intramedullary nail.

9. A telemetric orthopaedic implant comprising; (i) a strain gauge orientated at about +45° or at about −45° relative to a longitudinal axis of the implant; (ii) a recess adapted to receive said strain gauge(s); (iii) an electronic component electrically connected to at least a power supply, a first transmitter, a first receiver, and a first microprocessor; (iv) a recess adapted to receive said electronic component; (v) potting material to seal said recess(es); (vi) a power source electrically connected to said electronic component.

10. The telemetric orthopaedic implant of claim 9 which comprises at least one further strain gauge orientated at about 0° or at about 90° relative to the longitudinal axis of the implant.

11. The telemetric orthopaedic implant system of claim 9, wherein the recess for receiving the strain gauges and the electronic component is the same recess.

12. The telemetric orthopaedic implant system of claim 9, wherein there is a single recess.

13. The telemetric orthopaedic implant system of claim 12, wherein the single recess is located in the proximal portion of the implant.

14. The telemetric orthopaedic implant system of claim 9, wherein the telemetric orthopaedic implant is an intramedullary nail.

15. A method of monitoring fracture healing in a subject, said method comprising the steps of;
   (i) positioning a subject having a telemetric orthopaedic implant in a position suitable for applying a desired torque;
   (ii) applying the torque to the implant;
   (iii) interrogating at least one strain gauge provided within the implant and being orientated at about +45° or at about −45° relative to the longitudinal axis;
   (iv) correlating the strain with a reference fracture healing curve.

16. The method of claim 15, wherein the mechanical load is off-set axial compression and the at least one strain gauge being interrogated is orientated at about 0° or at about 90 relative to the longitudinal axis.

17. A method of measuring inter-fragmentary movement within a bone fracture, wherein the bone fracture is fixed with a fracture fixation device, said method comprising;
   (i) associating of a plurality of radio-opaque markers with the fractured bone or the fracture fixation device;
   (ii) positioning a calibration cage comprising a plurality of radio-opaque markers at known locations in relation to the fracture site;
   (iii) undertaking a radiographic examination of the fracture site, wherein the fracture site and the calibration cage are simultaneously x-rayed from at least two angles;
   (iv) generating a three-dimensional co-ordinate system based upon the location of the radio-opaque markers in the calibration cage;
   (v) comparing the three-dimensional location of the radio-opaque markers associated with the fractured bone or the fracture fixation device with the three-dimensional co-ordinate system.

\* \* \* \* \*